United States Patent
Bindra et al.

(10) Patent No.: US 8,430,892 B2
(45) Date of Patent: Apr. 30, 2013

(54) SURGICAL CLIP APPLIER HAVING A WIRELESS CLIP COUNTER

(75) Inventors: Manjit Singh Bindra, Mysore (IN); Prabhu Ramlingam, Mysore (IN)

(73) Assignee: Covidien LP, Mansfield, MA (US)

( * ) Notice: Subject to any disclaimer, the term of this patent is extended or adjusted under 35 U.S.C. 154(b) by 320 days.

(21) Appl. No.: 12/895,901

(22) Filed: Oct. 1, 2010

(65) Prior Publication Data

US 2011/0082474 A1    Apr. 7, 2011

Related U.S. Application Data

(60) Provisional application No. 61/248,944, filed on Oct. 6, 2009.

(51) Int. Cl.
*A61B 17/10* (2006.01)
(52) U.S. Cl.
USPC .......................................................... 606/143
(58) Field of Classification Search .................. 606/143
See application file for complete search history.

(56) References Cited

U.S. PATENT DOCUMENTS

| | | | |
|---|---|---|---|
| 4,242,902 A | | 1/1981 | Green |
| 4,712,549 A | * | 12/1987 | Peters et al. .................. 606/143 |
| 5,047,038 A | | 9/1991 | Peters |
| 5,529,235 A | | 6/1996 | Boiarski et al. |
| 5,535,934 A | | 7/1996 | Bpiarski et al. |
| 5,535,937 A | | 7/1996 | Boiarski et al. |
| 5,562,239 A | | 10/1996 | Boiarski et al. |

| | | |
|---|---|---|
| 2003/0009154 A1 | 1/2003 | Whitman |
| 2004/0230094 A1 | 11/2004 | Nakamura |
| 2007/0023476 A1 | 2/2007 | Whitman et al. |
| 2007/0118155 A1 | 5/2007 | Goldfarb et al. |
| 2007/0156017 A1 | 7/2007 | Lamprecht et al. |
| 2008/0164296 A1 | 7/2008 | Shelton et al. |
| 2008/0171909 A1 | 7/2008 | Onoda et al. |
| 2008/0197167 A1 | 8/2008 | Viola et al. |
| 2008/0243145 A1 | 10/2008 | Whitfield |

(Continued)

FOREIGN PATENT DOCUMENTS

| | | |
|---|---|---|
| EP | 0 085 931 A2 | 8/1983 |
| EP | 0 324 166 A2 | 7/1989 |

(Continued)

OTHER PUBLICATIONS

European Search Report corresponding to European Application No. EP 05 80 2686.5, completed Jan. 9, 2012; mailed Jan. 18, 2012; (3 Pages).

(Continued)

*Primary Examiner* — Melanie Tyson

(57) ABSTRACT

An apparatus for application of surgical clips to body tissue is provided and includes a housing, at least one handle a channel assembly, a clip carrier disposed within the channel assembly and a counter mechanism supported in at least one of the housing and the channel assembly. The counter mechanism is configured to transmit a change in status of the apparatus upon each actuation of the at least one handle. The counter mechanism includes a switch configured to output a signal upon actuation of the trigger, an encoder configured to output a bit sequence upon actuation of the switch, a radio frequency transmitter operable to convert the bit sequence into a radio frequency signal, and a transmitting antenna configured to transmit the radio frequency signal.

2 Claims, 20 Drawing Sheets

U.S. PATENT DOCUMENTS

| | | |
|---|---|---|
| 2008/0245841 A1 | 10/2008 | Smith et al. |
| 2008/0251568 A1 | 10/2008 | Zemlok et al. |
| 2008/0255418 A1 | 10/2008 | Zemlok et al. |
| 2010/0274262 A1 | 10/2010 | Schulz et al. |

FOREIGN PATENT DOCUMENTS

| | | |
|---|---|---|
| EP | 0 392 750 A1 | 10/1990 |
| EP | 0 598 529 A2 | 5/1994 |
| EP | 0 769 275 A1 | 5/1994 |
| EP | 0 685 204 A1 | 12/1995 |
| EP | 0 769 274 A1 | 4/1997 |
| EP | 1908423 | 4/2008 |
| EP | 2229895 | 9/2010 |
| JP | 2003 033361 A | 2/2003 |

OTHER PUBLICATIONS

The Extended European Search Report corresponding to European Application No. EP 12 15 1313.9, completed Mar. 20, 2012 and mailed Apr. 12, 2012; (5 Pages).

The Extended European Search Report corresponding to European Application No. EP 12 16 1291.5, completed Apr. 24, 2012 and mailed May 4, 2012; (5 pp.).

Extended European Search Report corresponding to EP 10252079.8, date of mailing is Mar. 17, 2011; date of completion of Search is Mar. 8, 2011 (3 Pages).

European Search Report dated May 20, 2011 for the corresponding application EP 10251737, date of completion May 9, 2011.

The Extended European Search Report corresponding to European Application No. EP 11250214.1, completed May 25, 2011; mailed Jun. 1, 2011; (3 Pages).

European Search Report corresponding to EP 05810218.7, mailed on May 20, 2011; completed on Apr. 18, 2011; 3 pages.

European Search Report corresponding to EP 05807612.6, mailed on May 20, 2011; completed on May 2, 2011; 3 pages.

The Extended European Search Report corresponding to European Application No. EP 12 16 2288.0, completed Jun. 4, 2012 and mailed Jul. 7, 2012; (6 Pages).

The Extended European Search Report corresponding to European Application No. EP 12 16 5891.8, completed Jun. 12, 2012 and mailed Jun. 20, 2012; (6 Pages).

The Extended European Search Report corresponding to European Application No. EP 12 16 4955.2, completed Aug. 23, 2012 and mailed Sep. 4, 2012; (5 pages).

\* cited by examiner

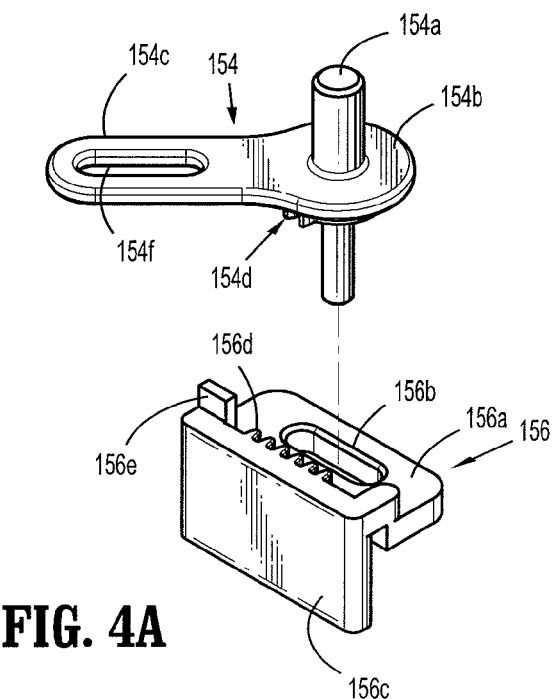
FIG. 4A
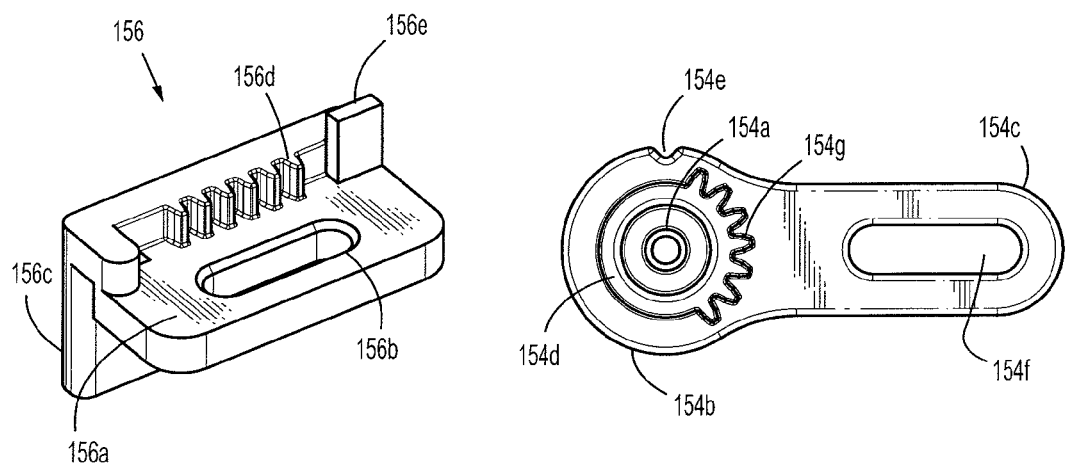
FIG. 4B  FIG. 4C

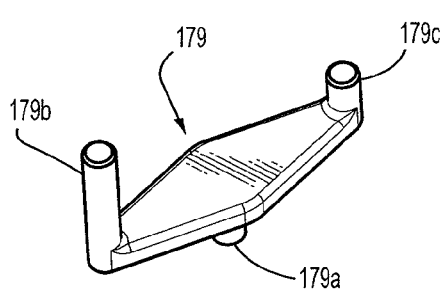 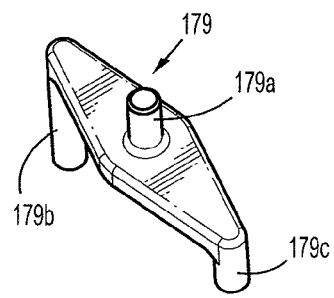
FIG. 4D  FIG. 4E
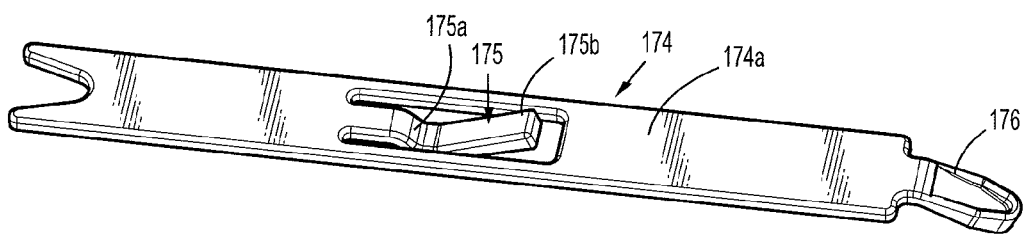
FIG. 4F
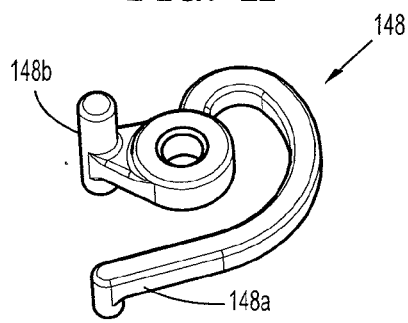
FIG. 4G
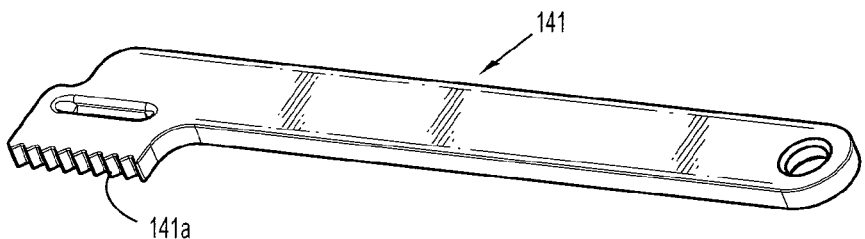
FIG. 4H

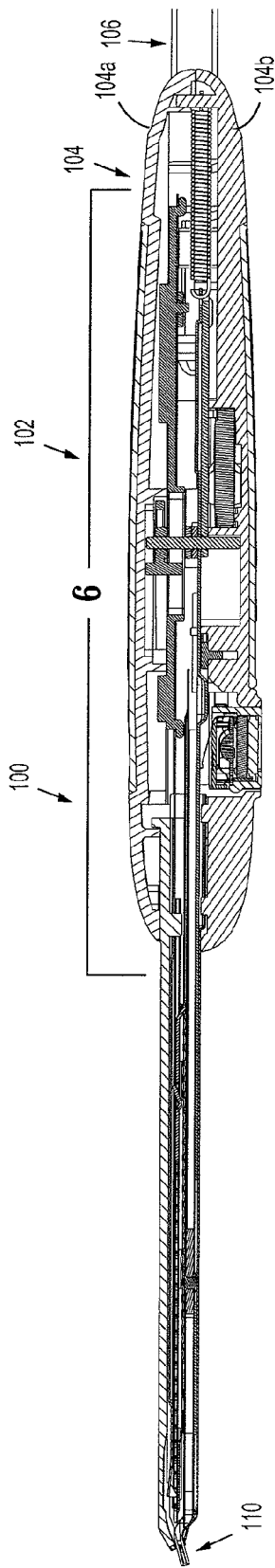
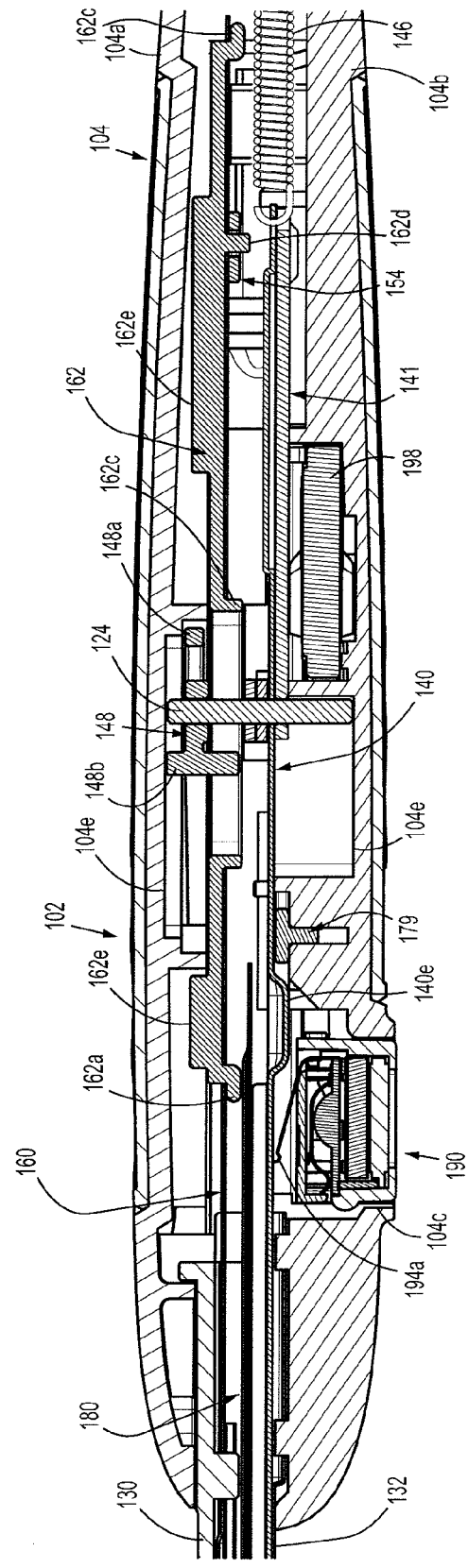
FIG. 5
FIG. 6

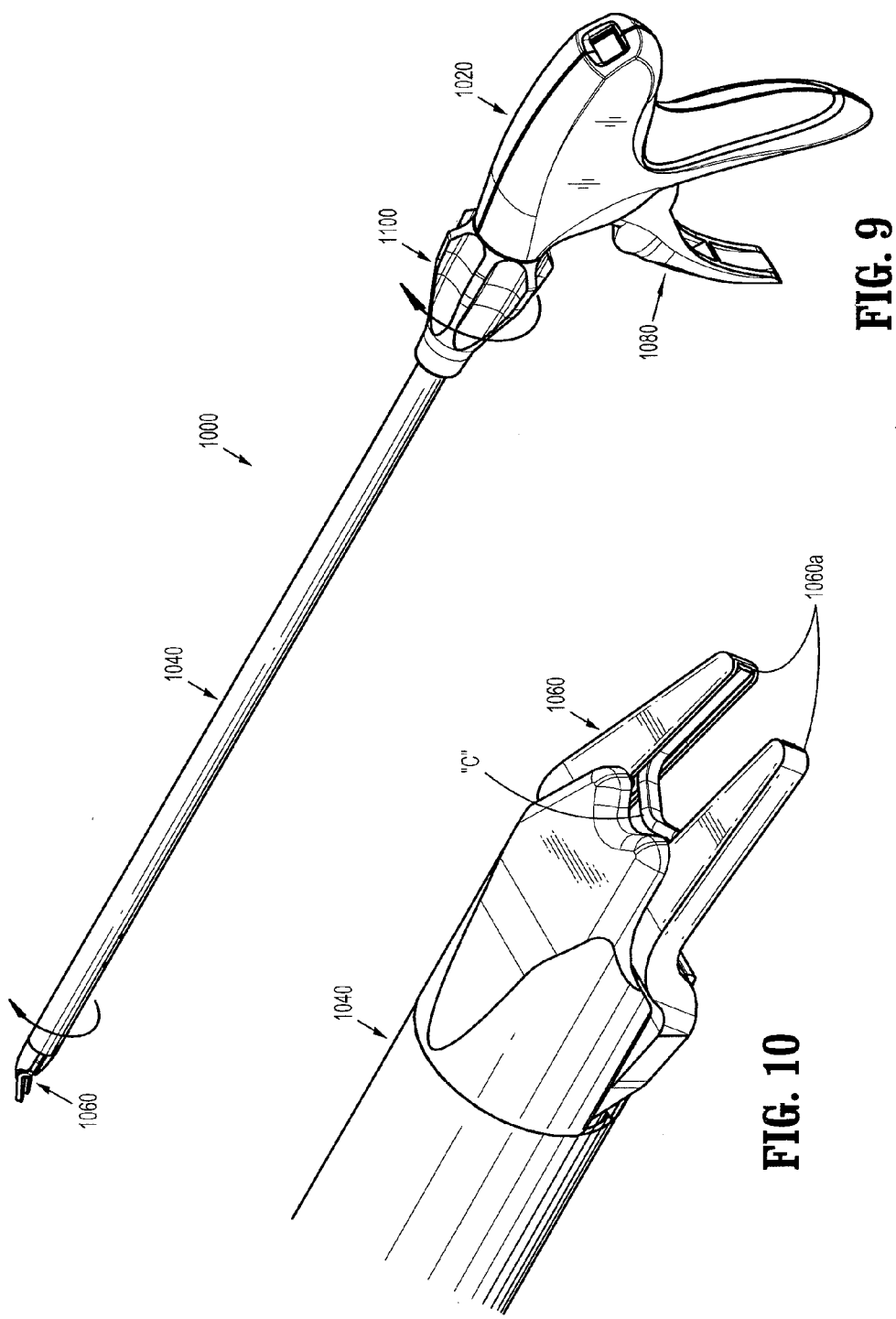

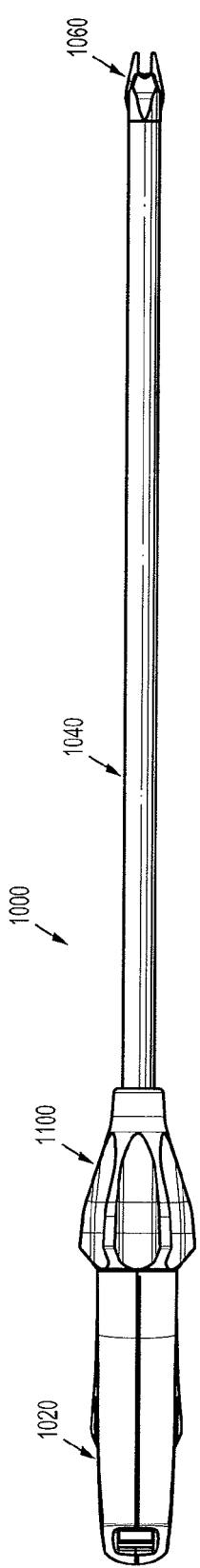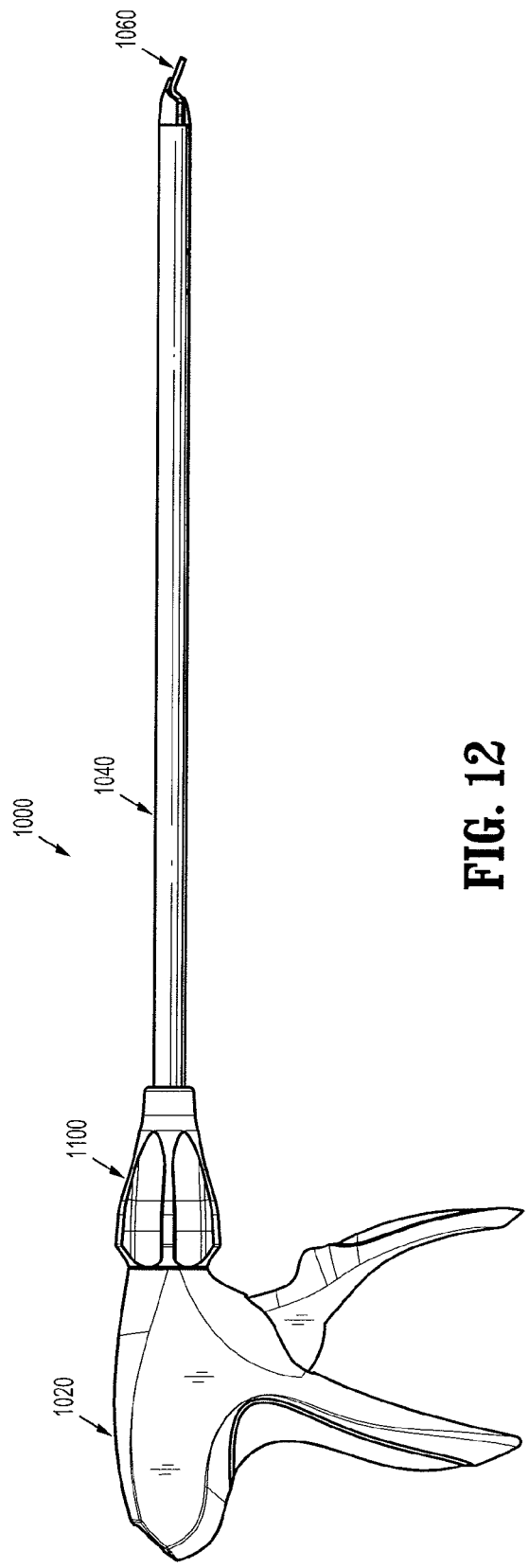
FIG. 11
FIG. 12

SURGICAL CLIP APPLIER HAVING A WIRELESS CLIP COUNTER

CROSS-REFERENCE TO RELATED APPLICATIONS

The present application claims the benefit of and priority to U.S. Provisional Application Ser. No. 61/248,944, filed on Oct. 6, 2009, the entire content of which is hereby incorporated by reference.

BACKGROUND

1. Technical Field

The present application relates to surgical instruments, and more particularly, to a surgical clip applier having a transmitter and remote display to count the number of clips in the surgical clip applier.

2. Discussion of Related Art

Surgical clip appliers are known in the art and have increased in popularity among surgeons by offering an alternative to conventional suturing of body tissues and vessels. Typical instruments are disclosed in U.S. Pat. No. 5,030,226 to Green et al. and U.S. Pat. No. 5,431,668 to Burbank III et al. These instruments generally provide a plurality of clips which are stored in the instrument and which are fed sequentially to the jaw mechanism at the distal end of the instrument upon opening and closing of the handles at the proximal end of the instrument. As the handles are closed, the jaws close to deform a clip positioned between the jaw members, and as the jaws are opened to release the deformed clip, a new clip is fed from the series to a position between the jaws. This process is repeated until all the clips in the series of clips have been used.

Endoscopic clip appliers are also known in the art for applying a single clip during an entry to the body cavity. Such single clip appliers are typically fabricated from a biocompatible material and are usually compressed over a vessel. Once applied to the vessel, the compressed clip terminates the flow of fluid therethrough. Endoscopic clip appliers that are able to apply multiple clips in endoscopic or laparoscopic procedures during a single entry into the body cavity are described in commonly-assigned U.S. Pat. Nos. 5,084,057 and 5,100,420 to Green et al., which are both incorporated by reference in their entirety. Another multiple endoscopic clip applier is disclosed in commonly-assigned U.S. Pat. No. 5,607,436 to Pratt et al., the contents of which is also hereby incorporated by reference herein in its entirety. These devices are typically, though not necessarily, used during a single surgical procedure. U.S. patent application Ser. No. 08/515,341 now U.S. Pat. No. 5,695,502 to Pier et al., the disclosure of which is hereby incorporated by reference herein, discloses a resterilizable surgical clip applier. The clip applier advances and forms multiple clips during a single insertion into the body cavity.

Application of clips may be complicated by a reduced field of view or reduced tactile feedback for the user at the proximal end of the device. It is therefore desirable to improve the operation of the instrument by providing indication to the user of the depletion of the clips contained in the loading unit. Conventional surgical clip applier or endoscopic clip appliers have a built in counter and display to provide such an indication. Due to the size of the clip appliers, the size of the display may be relatively small.

SUMMARY

The present disclosure relates to novel surgical clip appliers.

According to an aspect of the present disclosure, a surgical clip applier is provided including a housing; at least one handle pivotably connected to the housing; a channel assembly extending from the housing; a clip carrier disposed within the channel assembly and defining a channel and a plurality of windows therein; a plurality of clips slidably disposed within the channel of the clip carrier; and a counter mechanism supported in at least one of the housing and the channel assembly, wherein the counter mechanism is configured to transmit a change in status of the apparatus upon each actuation of the at least one handle.

The counter mechanism includes a switch configured to output a signal upon actuation of the at least one handle; an encoder configured to output a bit sequence upon actuation of the switch; a radio frequency transmitted operable to convert the bit sequence into a radio frequency signal; and a transmitting antenna configured to transmit the radio frequency signal.

According to another aspect of the present disclosure, an apparatus for application of surgical clips to body tissue is provided. The apparatus includes a handle assembly having a trigger; a shaft assembly extending distally from the handle assembly and defining a longitudinal axis; a plurality of surgical clips disposed within the shaft assembly; a jaw mounted adjacent a distal end portion of the shaft assembly, the jaw being movable between an open spaced-apart condition and a closed approximated condition; and a counter mechanism supported in the handle assembly, wherein the counter mechanism provides an indication when a surgical clip has been fired upon activation of the trigger.

The counter mechanism includes a switch configured to output a signal upon actuation of the trigger; an encoder configured to output a bit sequence upon actuation of the switch; a radio frequency transmitted operable to convert the bit sequence into a radio frequency signal; and a transmitting antenna configured to transmit the radio frequency signal.

According to another aspect of the present disclosure, a display unit is provided and includes a receiver configured to receive a radio frequency signal from the clip applier; a decoder configured to decode the radio frequency signal; a counter configured to provide a count of a number of clips; and a display driver operable to control a display based on the count provided by the counter.

The counter is a binary coded decimal counter that provides a binary coded signal to the display driver. The counter decrements the count of the number of clips when the receiver receives a radio frequency signal from the clip applier. The counter may also increment the count of the number of clips when the receiver receives a radio frequency signal from the clip applier.

The display has at least one seven segment light emitting diode.

The display unit further includes a a power on reset switch configured to reset the display when the count reaches a predetermined number.

According to another aspect of the present disclosure, a system for application of surgical clips to body tissue is provided and includes an apparatus for applying the surgical clip and a display unit configured receive the change in status of the apparatus upon each actuation of the at least one handle and display a count of the number of clips based on the change in status. The apparatus includes a housing; at least one handle pivotably connected to the housing; a channel assembly extending distally from the housing; a clip carrier disposed within the channel assembly and defining a channel and a plurality of windows therein; a plurality of clips slidably disposed within the channel of the clip carrier; and a counter mechanism supported in at least one of the housing and the channel assembly, wherein the counter mechanism is configured to transmit a change in status of the apparatus upon each actuation of the at least one handle.

According to another aspect of the present disclosure, a system for application of surgical clips to body tissue is provided and includes an apparatus for applying the surgical clip and a display unit configured receive the change in status of the apparatus upon each actuation of the at least one handle and display a count of the number of clips based on the change in status. The apparatus includes a handle assembly having a trigger; a shaft assembly including a housing extending distally from the handle assembly and defining a longitudinal axis; a plurality of surgical clips disposed within the shaft assembly; a jaw mounted adjacent a distal end portion of the shaft assembly, the jaw being movable between an open spaced-apart condition and a closed approximated condition; and a counter mechanism supported in the handle assembly, wherein the counter mechanism provides an indication when a surgical clip has been fired upon activation of the trigger.

The display unit displays a number of clips remaining in the apparatus or the number of clips applied by the apparatus.

BRIEF DESCRIPTION OF THE DRAWINGS

The present clip applier will be more fully appreciated as the same becomes better understood from the following detailed description when considered in connection with the following drawings, in which:

FIG. 4A is an exploded perspective view of a bell crank gear and accelerator rack assembly of the surgical clip applier of FIGS. 1-4;

FIG. 4B is a perspective view of the accelerator rack of the surgical clip applier of FIGS. 1-4;

FIG. 4C is a view of the bell crank gear of the surgical clip applier of FIGS. 1-4;

FIG. 4D is a top, perspective view of a pivot arm of the surgical clip applier of FIGS. 1-4;

FIG. 4E is a bottom, perspective view of the pivot arm of FIG. 4D;

FIG. 4F is a top, perspective view of a clip follower of the surgical clip applier of FIGS. 1-4;

FIG. 4G is a perspective view of an audible/tactile indicator of the surgical clip applier of FIGS. 1-4;

FIG. 4H is a perspective view of a rack member of the surgical clip applier of FIGS. 1-4;

FIG. 5 is a longitudinal cross-sectional view of the surgical clip applier of FIGS. 1-4, illustrating the surgical clip applier in an unactuated condition;

FIG. 6 is an enlarged view of the indicated area of detail of FIG. 5;

FIG. 9 is a rear, perspective view of the clip applier of FIG. 8 illustrating a rotation of a shaft assembly thereof;

FIG. 10 is a front, perspective view of a distal end of the shaft assembly of the clip applier of FIGS. 8 and 9;

FIG. 11 is a top, plan view of the clip applier of FIGS. 8 and 9;

FIG. 12 is a side, elevational view of the clip applier of FIGS. 8 and 9;

DETAILED DESCRIPTION OF EMBODIMENTS

Figure 1:
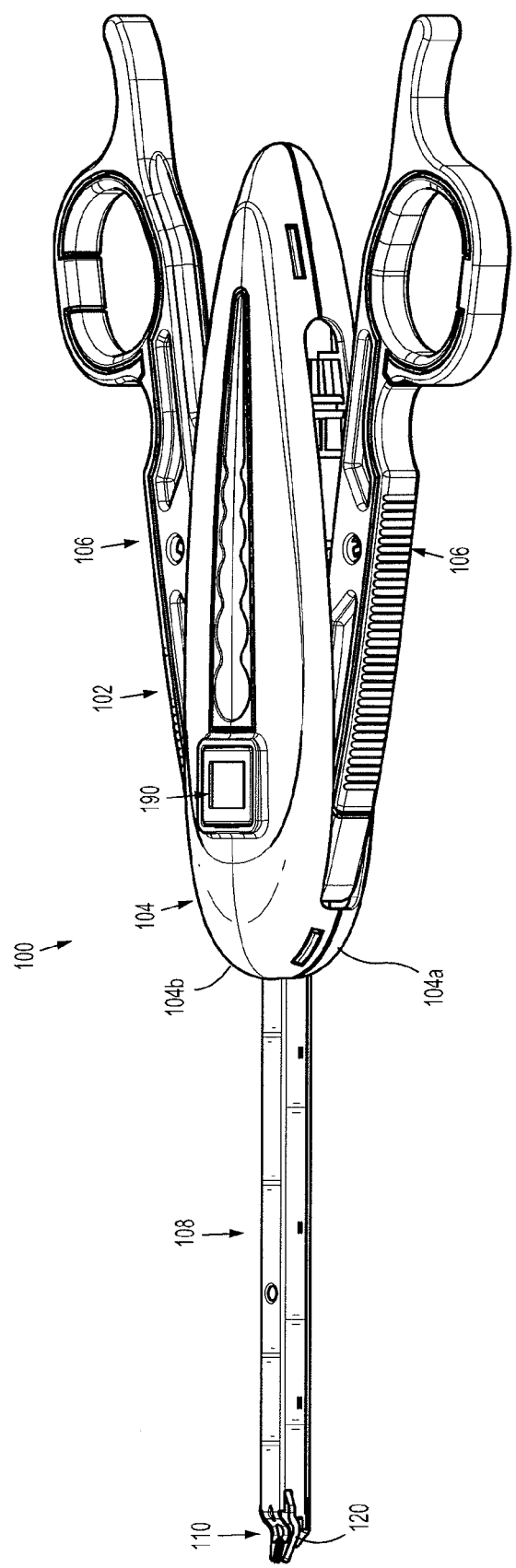
FIG. 1 is a perspective view of a surgical clip applier according to an embodiment of the present disclosure.

Embodiments of surgical clip appliers in accordance with the present disclosure will now be described in detail with reference to the drawing figures wherein like reference numerals identify similar or identical structural elements. As shown in the drawings and described throughout the following description, as is traditional when referring to relative positioning on a surgical instrument, the term "proximal" refers to the end of the apparatus which is closer to the user and the term "distal" refers to the end of the apparatus which is further away from the user.

There are various types of surgical clip appliers that can be used in conjunction with the embodiments described herein. Such clip appliers are described in U.S. patent application Ser. No. 12/406,345, filed on Mar. 18, 2009, entitled "Endoscopic Surgical Clip Applier"; U.S. Provisional Patent Application Ser. No. 61/091,485, filed Aug. 25, 2008; and U.S. Provisional Patent Application Ser. No. 61/092,804, filed Aug. 29, 2008, the content of each of which being incorporated by reference herein in their entirety.

Referring now to FIGS. 1-6, a surgical clip applier in accordance with an embodiment of the present disclosure is generally designated as 100. Surgical clip applier 100 generally includes a handle assembly 102 including a housing 104 having an upper housing half 104a and lower housing half 104b. Handle assembly 102 further includes a pair of handles 106 pivotably secured to housing 104 and extending outwardly therefrom. A channel assembly 108 is fixedly secured to housing 104 and extends outwardly therefrom, terminating in a jaw assembly 110.

As seen in FIGS. 1-7, housing halves 104a and 104b of clip applier 100 fit together by snap fit engagement with one another. Housing 104 defines a window 104c formed in lower housing half 104b for supporting a counter mechanism 190, as will be discussed in greater detail below with reference to FIG. 17. Housing 104 is formed of a suitable plastic material.

Figure 4:
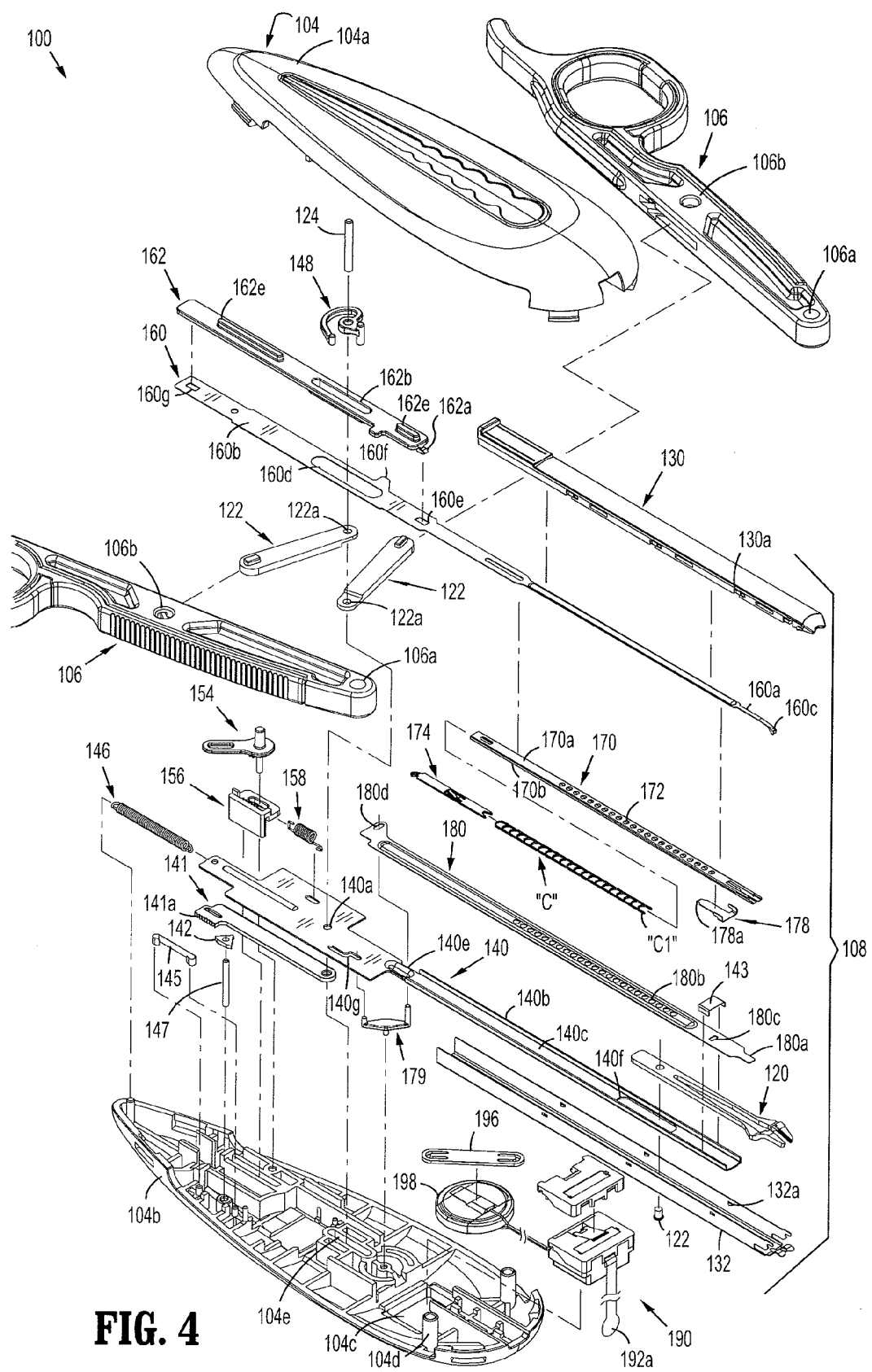
FIG. 4 is an exploded perspective view of the surgical clip applier of FIGS. 1-3.

As seen in FIG. 4, handles 106 are secured to housing 104 by handle pivot posts 104d extending from lower housing half 104b and into respective apertures 106a formed in handles 106. Handle assembly 102 includes a link member 122 pivotally connected to each handle 106 at a pivot point 106b formed in a respective handle 106. A distal end 122a of each link member 122 is pivotally connected to a pivot point 140a formed in a drive channel 140 via a drive pin 124. Each end of drive pin 124 is slidably received in an elongate channel 104e formed in a respective upper and lower housing half 104a, 104b. In use, as will be described in greater detail below, as handles 106 are squeezed, link members 122 push drive channel 140 distally via drive pin 124.

Channel assembly 108 includes a channel or cartridge cover 130 and an outer or lower channel 132 each having a proximal end retained in housing assembly 102, between upper and lower housing halves 104a, 104b. Cartridge cover 130 includes at least one retention element 130a configured and adapted to selectively engage, in a snap-fit engagement, a complementary or corresponding retention element 132a provided on outer channel 132.

As seen in FIGS. 4 and 6, clip applier 100 includes a clip pusher bar 160 slidably disposed beneath cartridge cover 130. Pusher bar 160 includes a distal end 160a defining a pusher 160c configured and adapted to selectively engage/move a distal-most clip "C1" stored in surgical clip applier 100. Pusher bar 160 further includes a proximal end 160b defining a proximal window 160d therein for slidably receiving drive pin 124 therein. Pusher bar 160 further defines a distal window 160e therein for operative engagement with a stabilizer 162, as will be discussed in greater detail below. Pusher bar 160 also includes a fin 160f projecting from a side edge thereof and located in relative close proximity to proximal window 160d.

Clip applier 100 further includes a stabilizer 162 configured to overlie and engage pusher bar 160. Stabilizer 162 includes a distal tab 162a configured to engage distal window 160e of pusher bar 160, an elongate window 162b defined therein at a location to substantially overlie and be in registration with proximal window 160d formed in pusher bar 160. Stabilizer 162 further includes a nub 162c extending from a bottom surface thereof, at a location proximal of elongate window 162b, which is configured and dimensioned for receipt in a proximal-most aperture 160g formed in pusher bar 160. As seen in FIGS. 4 and 6, stabilizer 162 further includes a pair of tabs 162e extending from a top surface thereof, at a proximal and a distal location, which are configured and dimensioned for receipt in respective channels formed in upper housing half 104a.

As seen in FIGS. 4 and 4A-4C, clip applier 100 further includes a motion multiplier system having a bell crank gear 154 pivotally supported in housing 104 and an accelerator housing 156 slidably supported in housing 104. Bell crank gear 154 includes a pivot pin 154a configured for pivotable connection to housing 104, a disk-like body 154b supported on pivot pin 154a, an arm 154c extending radially from disk-like body 154b, and a spur gear 154d supported on pivot pin 154a or integrally formed therewith and located adjacent disk-like body 154b. Bell crank gear 154 defines a detent or notch 154e (see FIG. 4C) formed in a side edge of disk-like body 154b and a longitudinally oriented slot 154f formed in arm 154c. Spur gear 154d of bell crank gear 154 defines a plurality of gear teeth 154g formed in a side edge thereof and may be a sector gear as best shown in FIG. 4C.

Bell crank gear 154 is a common part for each of the small, medium and large scaled clip appliers 100. Notch 154e formed in side edge of disk-like body 154b of bell crank gear 154 is provided for the assembly of the large scaled clip applier. The larger scaled clip applier requires a greater pusher stroke and therefore a greater degree of rotation of bell crank gear 154. Due to the greater rotation of bell crank gear 154, disk-like body 154b will contact a tab 156e (see FIGS. 4A and 4B) extending from an accelerator rack 156. During assembly, bell crank gear 154 is rotated until notch 154e contacts tab 156e of accelerator rack 156.

With continued reference to FIGS. 4 and 4A-4C, accelerator rack 156 of motion multiplier system includes a base wall 156a defining an elongate, longitudinally extending slot 156b formed therein, for slidable receipt of pivot pin 154a of bell crank gear 154. Accelerator rack 156 includes a side wall 156c projecting in opposite directions from a side edge of base wall 156a, and a gear rack 156d formed in side wall 156c and in registration or alignment with slot 156b of base wall 156a. Gear rack 156d is configured for engagement with gear teeth 154g of spur gear 154d of bell crank gear 154.

Clip applier 100 further includes a biasing member 158 interconnecting accelerator rack 156 and drive channel 140.

As seen in FIG. 6, slot 154f of arm 154c of bell crank gear 154 is configured and dimensioned to slidably and rotatably receive a nub 162d of stabilizer 162 therein. In use, as drive channel 140 is translated distally, biasing member 158, which interconnects drive channel 140 and accelerator rack 156, subsequently moves accelerator rack 156 distally. As accelerator rack 156 is moved distally, since nub 162d of stabilizer 162 rides in slot 154f of arm 154c of bell crank gear 154, accelerator rack 156 causes bell crank gear 154 to rotate and push stabilizer 162 and, in turn, pusher bar 160 distally.

Clip applier 100 further includes a clip carrier 170 disposed within channel assembly 108 and beneath pusher bar 160. Clip carrier 170 is generally a box-like structure having an upper wall 170a, a pair of side walls 170b and a lower wall 170c defining a channel 170d therethrough. Clip carrier 170 includes a plurality of spaced apart windows 172 formed in upper wall 170a and extending longitudinally along a length thereof. Clip carrier 170 includes an elongate window (not shown) formed in lower wall 170c and extending longitudinally along a length thereof.

As seen in FIG. 4, a stack of surgical clips "C" is loaded and/or retained within the channel (not shown) of clip carrier 170 in a manner so as to slide therewithin and/or therealong. The channel is configured and dimensioned to slidably retain a stack or plurality of surgical clips "C" in tip-to-tail fashion therewithin.

As seen in FIGS. 4 and 4F, clip applier 100 further includes a clip follower 174 slidably disposed within the channel of clip carrier 170. As will be discussed in greater detail below, clip follower 174 is positioned behind the stack of surgical clips "C" and is provided to urge the stack of clips "C" forward during an actuation of clip applier 100. Clip follower 174 is actuated by the reciprocating forward and backward motion of wedge plate 180.

As seen in FIG. 4F, clip follower 174 includes body portion 174a defining a plane, a distal tab 175 extending substantially upwardly and rearwardly from body portion 174a, and a proximal tab 176 extending substantially downwardly and rearwardly from body portion 174a. Distal tab 175 includes a distal portion 175a extending downwardly below the plane defined by body portion 174a and a proximal portion 175b extending upwardly above the plane defined by body portion 174a.

Proximal portion 175b of distal tab 175 is configured and dimensioned to selectively engage windows 172 formed in upper wall 170a of clip carrier 170. In use, engagement of proximal portion 175b of distal tab 175 of clip follower 174 in a window 172 formed in upper wall 170a of clip carrier 170 prevents clip follower from traveling or moving in a proximal direction.

Proximal tab 176 is configured and dimensioned to selectively engage windows 180b formed in wedge plate 180. In use, engagement of proximal tab 176 of clip follower 174 in a window 180b formed in wedge plate 180 allows for clip follower 174 to be advanced or moved distally upon a distal movement of wedge plate 180.

As seen in FIG. 4, clip applier 100 further includes a wedge plate 180 slidably disposed within handle assembly 102 and channel assembly 108. Wedge plate 180 is positioned or disposed below clip carrier 170. Wedge plate 180 includes a substantially tapered distal end 180a for selective operative interposition between jaws 120. Wedge plate 180 defines a plurality of spaced apart windows or apertures 180b extending longitudinally along a length thereof and formed in a raised section thereof, a distal window or aperture 180c located distal of apertures 180b, and a proximal-most transversely oriented slot 180d located proximal of aperture 180c.

As seen in FIG. 4, clip applier 100 includes a distal lockout 178 supported by cartridge cover 130. Distal lockout 178 includes a tail or tab 178a extending substantially rearwardly and downwardly and being configured and dimensioned for receipt in distal window or aperture 180c of wedge plate 180.

As seen in FIGS. 4, 4D, 4E and 6, clip applier 100 includes a wedge plate motion reversing mechanism, in the form of a pivot arm 179, pivotally supported in lower housing half 104b of housing 104 for transmitting the translation of drive channel 140 to a reverse translation of wedge plate 180. Pivot arm 179 includes a pivot boss 179a configured for pivotable connection to housing 104, a first stem or finger 179b provided at one end of pivot arm 179 and extending in a direction opposite to pivot boss 179a, and second stem or finger 179c provided at a second end of pivot arm 179 and extending in a direction opposite to pivot boss 179a. First stem or finger 179b is configured and adapted for engagement in proximal-most slot 180d of wedge plate 180. Second stem or finger 179c is configured for engagement in a slot 140g formed in drive channel 140 which is connected in a window 140g defined in a drive channel 140. Slot 140g includes a longitudinally extending distal portion and a longitudinally extending proximal portion that are axially and transversely offset from one another, and a transverse portion interconnecting the distal and proximal portions.

In use, as drive channel 140 is moved distally, after a dwell period (i.e., the length of the longitudinally extending distal portion of slot 140g of drive channel 140), second stem or finger 179c is moved in a distal direction, rotating pivot arm 179 and thereby moving first stem or finger 179b in a second direction. As first stem or finger 179b is moved in the second direction, first stem or finger 179b pulls wedge plate 180 out from between jaws 120 urges against as well as urges or pushes proximally against fin 160f of pusher 160 to move pusher 160 in a proximal direction so that pusher bar 160c thereof is removed from between jaws 120, and vice-versa. As wedge plate 180 is moved in a distal direction, as seen n FIG. 17, distal end 180a of wedge plate 180 cams against an inner surface of jaws 120 to thereby maintain jaws 120 spaced apart from one another.

As seen in FIGS. 4 and 6, clip applier 100 includes a drive channel 140 reciprocally supported in and extending between housing 104 of handle assembly 102 and channel assembly 108. A proximal end of drive channel 140 is supported between upper and lower housing halves 104a, 104b of housing 104 and a distal end of drive channel 140 is supported between cartridge cover 130 and outer channel 132 of channel assembly 108, at a location below wedge plate 180.

A distal end of drive channel 140 is a substantially U-shaped channel including a pair of spaced apart side walls 140b extending from a backspan 140c thereof, in a direction away from outer channel 132 and toward cartridge cover 130. Drive channel 140 further defines a drive pin recess 140a formed in backspan 140c for pivotally receiving drive pin 124 therethrough. Drive channel 140 further defines a nub 140e projecting from backspan 140c at a location distal of drive pin recess 140a. Drive channel 140 further defines a reciprocation limiting slot 140f formed in backspan 140c at a location distal of slot 140e.

As seen in FIG. 4, clip applier 100 includes a drive channel strap 143 secured to drive channel 140. Strap 143 is secured to uprights 140b of drive channel 140 so as to extend transversely thereacross. Strap 143 is secured to drive channel 140 at a location distal of reciprocation limiting slot 140f. Strap 143 is secured to drive channel 140 such that wedge plate 180 extends beneath strap 143 and above jaws 120.

As seen in FIGS. 4, 4G and 6, clip applier 100 further includes an audible/tactile indicator 148 connected to drive channel 140 via drive pin 124. Indicator 148 includes a resilient finger 148a and a pair of bosses 148b. In use, as will be described in greater detail below, as clip applier 100 is actuated and drive channel 140 is reciprocated, first resilient finger 148a of indicator 148 interacts with corresponding complementary structure or ledge (not shown) provided in clip applier 100 to create an audible and/or a tactile feedback to the user. Bosses 148b of indicator 148 ride within channel 104e formed in upper housing half 104a and provide support to indicator 148 to prevent indicator 148 from rotating.

As seen in FIGS. 4 and 6, clip applier 100 further includes a biasing member 146, in the form of a tension spring, operatively secured to and between a proximal end of drive channel 140 and housing 104, tending to maintain drive channel 140 in a retracted or proximal-most position. Biasing member 146 functions to retract or facilitate retraction of drive channel 140 following formation of a clip "C" positioned between jaws 120.

As seen in FIGS. 4 and 4H, a proximal end of drive channel 140 includes a ratchet rack member 141 secured to drive pin 124 and movable with drive channel 140. Ratchet rack member 141 is configured and adapted to engage with a ratchet pawl 142 supported in housing 104. Rack member 141 and pawl 142 define a ratchet mechanism 144. In use, as drive channel 140 is moved axially, rack member 141 is also moved. Rack member 141 defines a series of rack teeth 141a having a length which allows pawl 142 to reverse and advance back over rack member 141 when rack member 141 changes between proximal and distal movement as drive channel 140 reaches a proximal-most or distal-most position.

Pawl 142 is pivotally connected to lower housing half 104b by a pawl pin 147 at a location wherein pawl 142 is in substantial operative engagement with rack member 141. Pawl 142 is engageable with rack member 141 to restrict longitudinal movement of rack member 141 and, in turn, drive channel 140. Ratchet mechanism 144 further includes a pawl spring 145 configured and positioned to bias pawl 142 into operative engagement with rack member 141. Pawl spring 145 functions to maintain the teeth of pawl 142 in engagement with the teeth 141a of rack member 141, as well as to maintain pawl 142 in a rotated or canted position.

As seen in FIGS. 1-4, clip applier 100 includes a pair of jaws 120 mounted on or at a distal end of channel assembly 108 and actuatable by handles 106 of handle assembly 102. Jaws 120 are formed of a suitable biocompatible material such as, for example, stainless steel or titanium.

Jaws 120 are mounted in a distal end of drive channel 140 via a rivet 122 or the like extending through reciprocation limiting slot 140f of drive channel 140 such that jaws 120 are longitudinally stationary relative to outer channel 132 and drive channel 140.

Figure 1A:
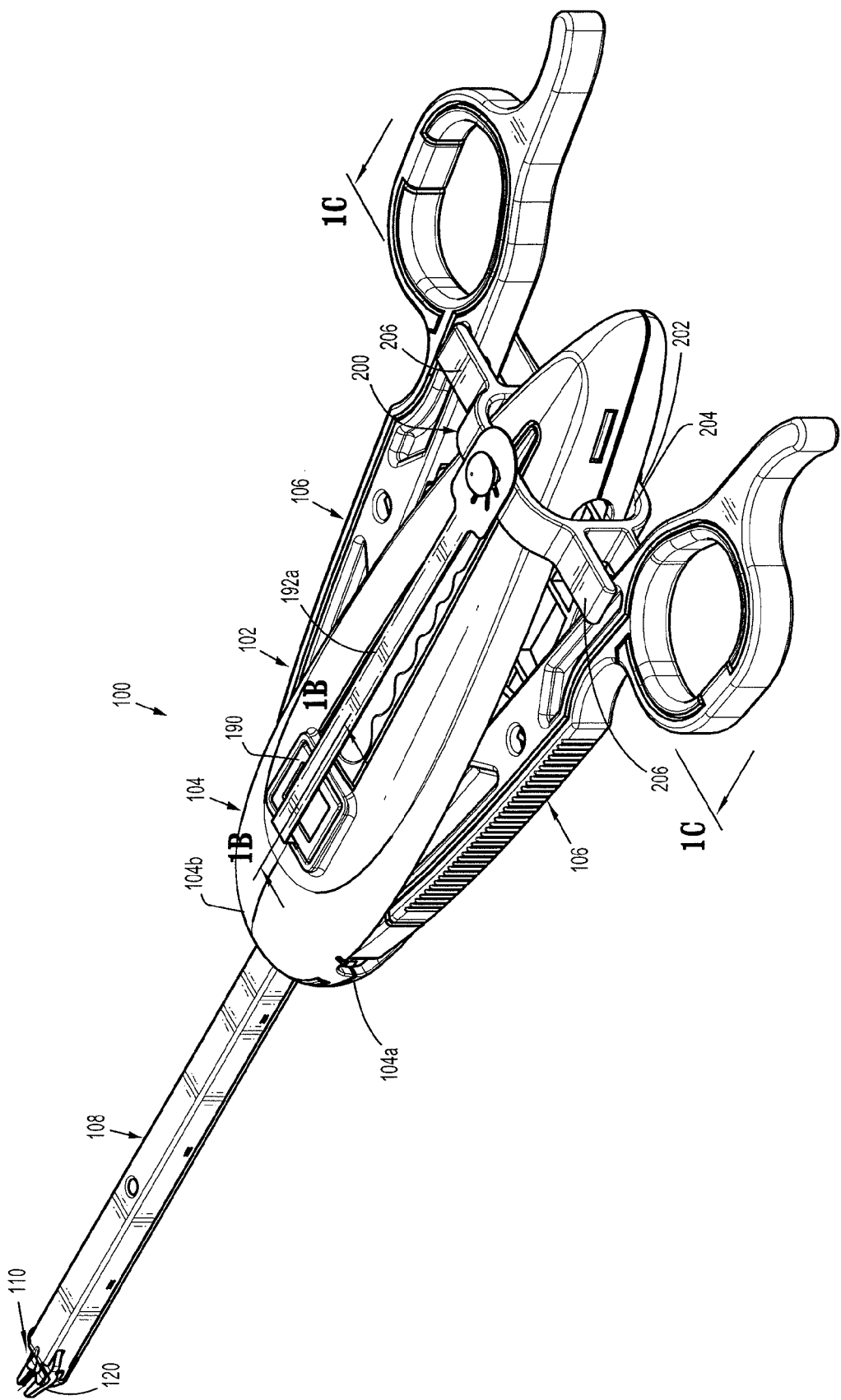
FIG. 1A is a rear, perspective view of the surgical clip applier of FIG. 1, shown with a shipping wedge in position.
Figure 1B:
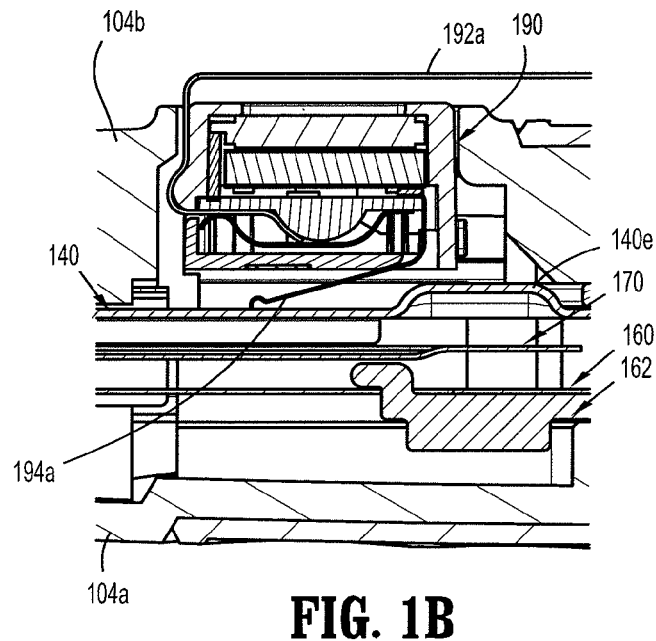
FIG. 1B is a cross-sectional view as taken through 1B-1B of FIG. 1A.

As seen in FIGS. 1-4 and 6, clip applier 100 further includes a counter mechanism 190 supported in housing 104 of handle assembly 102. Counter mechanism 190 will be described in more detail hereinbelow with reference to FIG. 17. Counter mechanism 190 includes a tab 192a, made from PVC, disposed between battery or energy source 198 and a contact 194a of switch 194 or between the contacts 194a of switch 194 to prevent the battery or energy source 198 from becoming drained during storage. As seen in FIGS. 1A and 1B, tab 192a extends out of housing 104 of clip applier 100 in order to allow for easy removal of the tab therefrom. Once the tab 192a is removed, battery or energy source 198 comes into electrical contact with the contact 194a of switch 194 or between the contacts 194a of the switch 194. Counter mechanism 190 is actuated by nub 140e formed in drive channel 140. In use, as seen in FIG. 6, as drive channel 140 is driven forward, nub 140e thereof engages contact 194a causing contact 194a to complete a circuit. In a further embodiment, as seen in FIG. 4 above, clip applier 100 may be provided with a strap 196 configured to secure energy source 198 to housing 104.

Clip applier 100 includes a wireless clip counter mechanism 800, as will be described in greater detail below and shown in FIGS. 17-19.

Figure 1C:
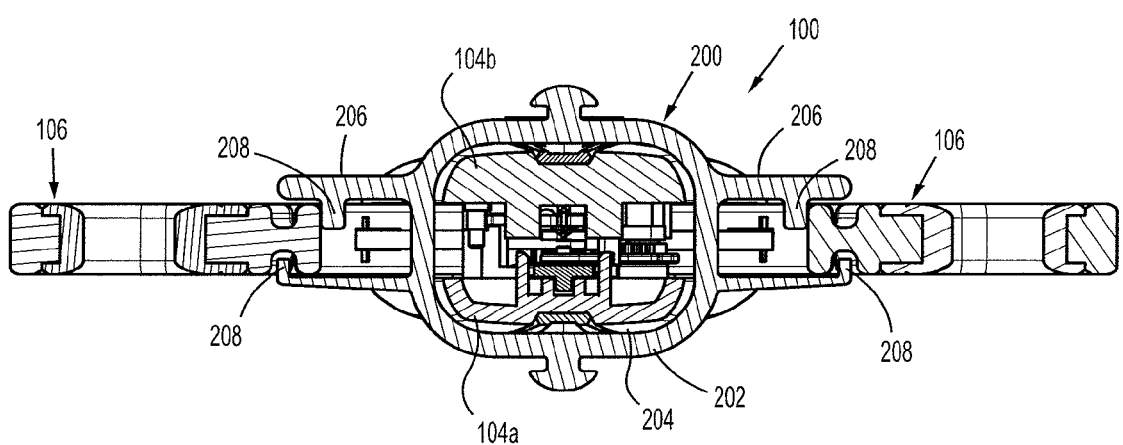
FIG. 1C is a cross-sectional view as taken through 1C-1C of FIG. 1A.
Figure 2:
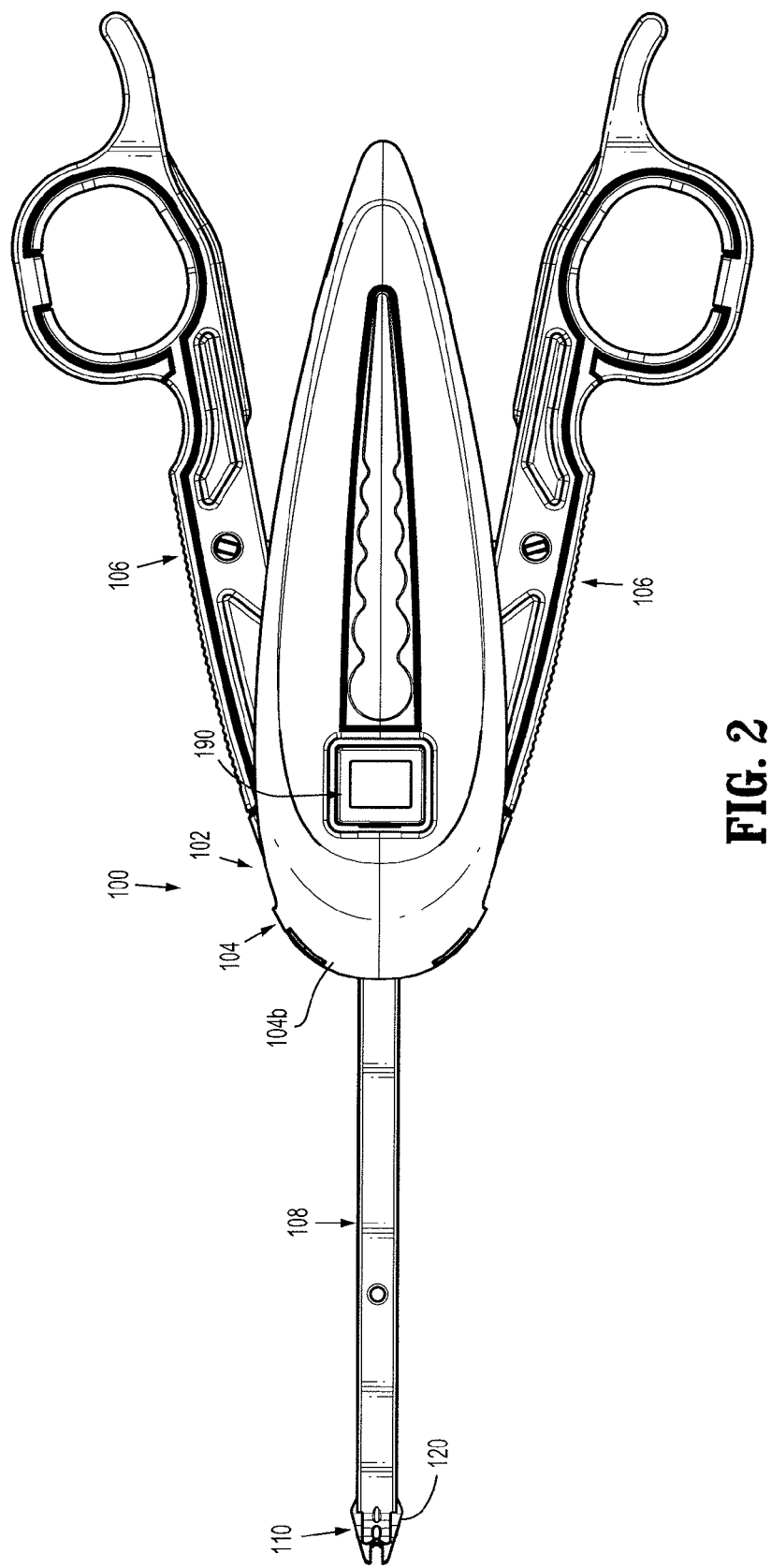
FIG. 2 is a top, plan view of the surgical clip applier of FIG. 1.
Figure 3:
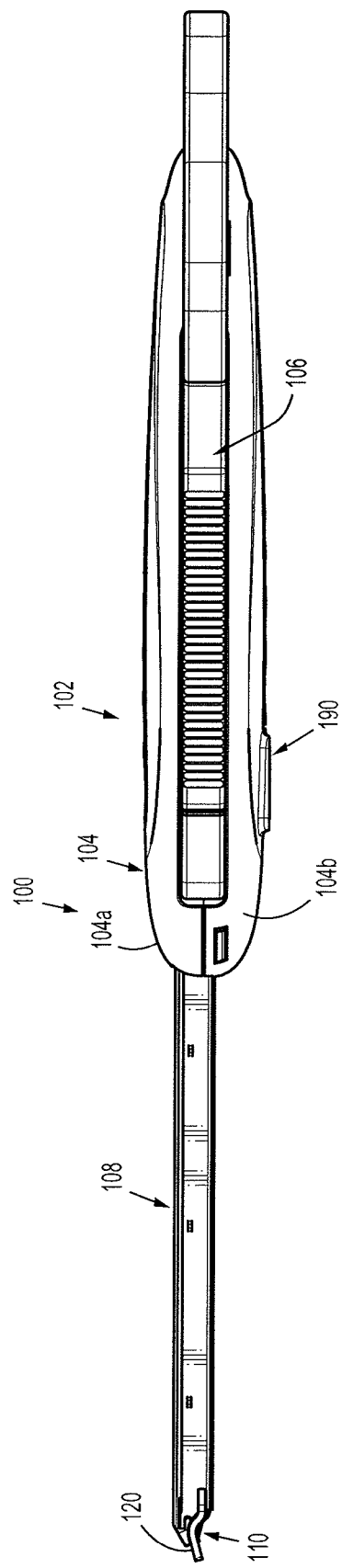
FIG. 3 is a side, elevational view of the surgical clip applier of FIGS. 1 and 2.

As seen in FIGS. 1A and 1C, clip applier 100 includes a shipping wedge 200 supported on housing 104 and interposed between handles 106. Shipping wedge 200 functions to maintain handles 106 spaced apart or un-squeezed during a shipment and/or storage of clip applier 100. Shipping wedge 200 is connected to tab 192a of counter mechanism 190, such that in order for an end user to use clip applier 100, the end user must remove shipping wedge 200 thereby also removing tab 192a to activate counter mechanism 190.

As seen in FIGS. 1A and 1C, shipping wedge 200 includes a body portion 202 in the form of a collar, defining a passage 204 configured and dimensioned for receipt of a portion of housing 104 therein. Shipping wedge 200 includes uprights 206 extending outwardly from opposed sides of body portion 202 and being configured to receive handles 106 therein. Shipping wedge 200 further includes tabs 208 extending inwardly from opposed sides of uprights 206. Tabs 208 of shipping wedge 200 are configured and dimensioned to engage with handles 106 when shipping wedge 200 is properly secured to clip applier 100.

Figure 7:
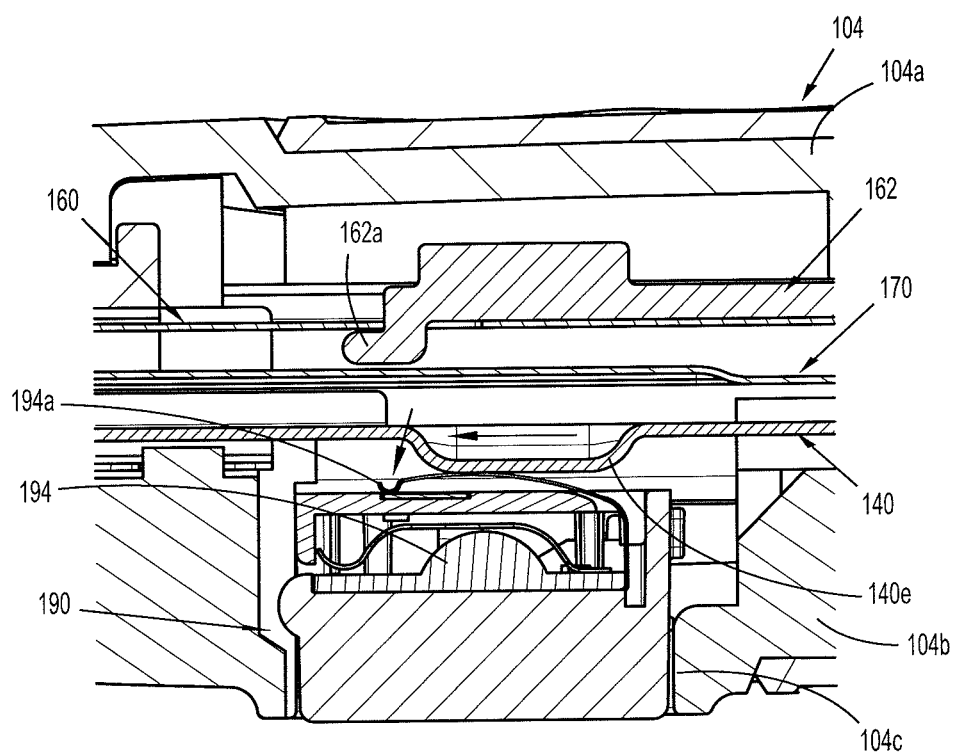
FIG. 7 is an enlarged, cross-sectional view illustrating an actuation of a counter mechanism of the surgical clip applier of FIGS. 1-3.
Figure 8:
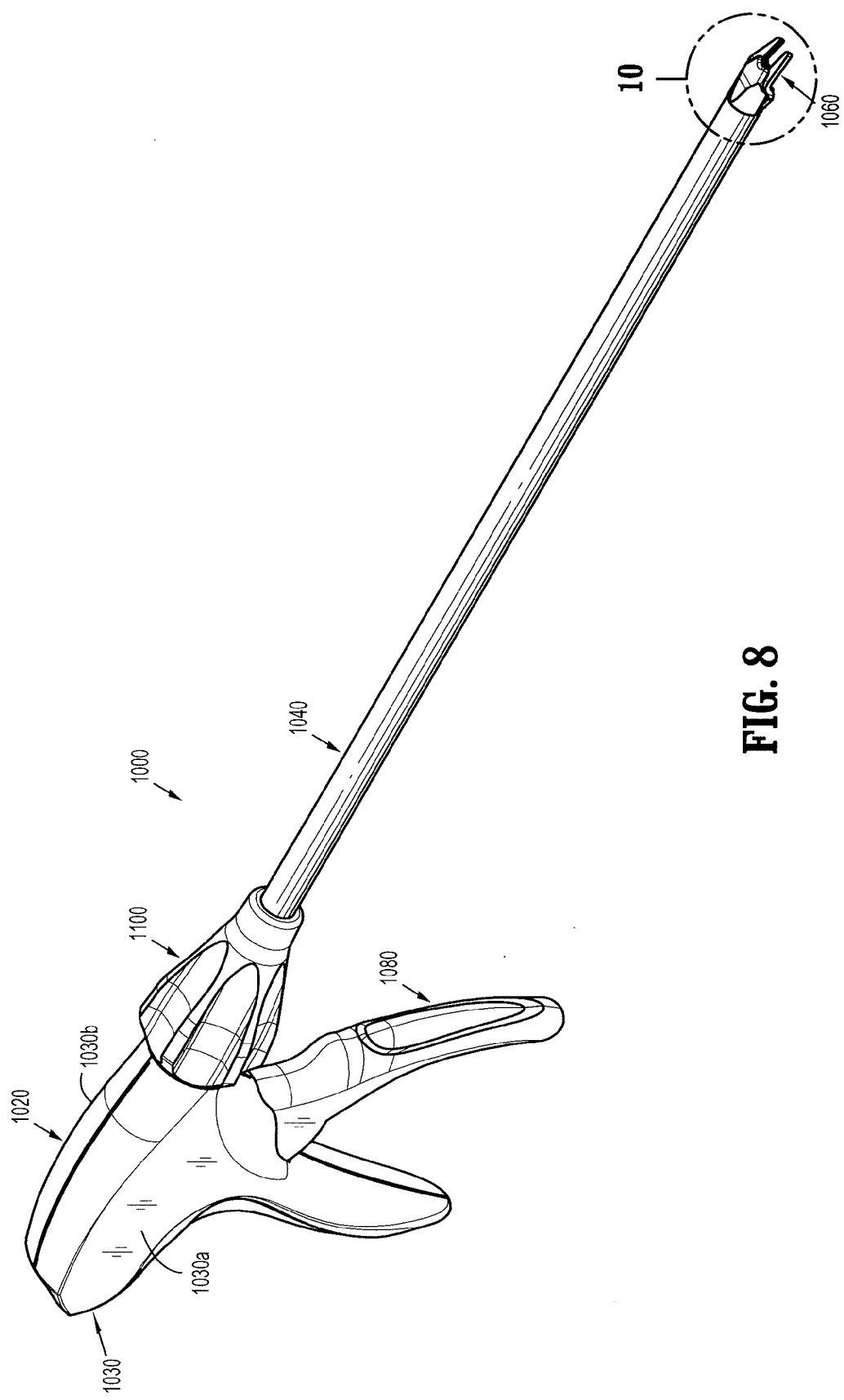
FIG. 8 is a front, perspective view of a surgical clip applier according to another embodiment of the present disclosure.

With continued reference to FIG. 7, during the further squeezing of handles 106, with tab 192a removed from counter mechanism 190, as drive channel 140 is advanced distally, nub 140e thereof engages contact 194a of switch 194 thereby completing a circuit and causing counter mechanism 190 to perform a function, as described above.

Referring now to FIGS. 8-12, a surgical clip applier in accordance with an embodiment of the present disclosure is generally designated as 1000. Clip applier 1000 includes a handle assembly 1020 and an endoscopic portion including a shaft assembly 1040 extending distally from handle assembly 1020.

Shaft assembly 1040 has an outer diameter of about 10 mm. Shaft assembly 1040 may have various elongated or shortened lengths depending on intended use, such as, for example, in bariatric surgery.

As seen in FIGS. 8-12, surgical clip applier 1000 includes a pair of jaws 1060 mounted on a distal end of shaft assembly 1040 and actuatable by a trigger 1080 of handle assembly 1020. Jaws 1060 are formed of a suitable biocompatible material such as, for example, stainless steel or titanium and define a channel 1060a therebetween for receipt of a surgical clip "C" therein. When jaws 1060 are in an open or un-approximated condition relative to each other, a width of jaws 1060 measures greater than an outer diameter of shaft assembly 1040.

Jaws 1060 are mounted in the distal end of shaft assembly 1040 such that they are longitudinally stationary relative thereto. A knob 1100 may be rotatably mounted on a distal end of handle assembly 1020 and affixed to shaft assembly 1040 to transmit and/or provide 360° rotation to shaft assembly 1040 and jaws 1060 about a longitudinal axis thereof (see FIG. 16).

Referring now to FIGS. 8-12, handle assembly 1020 of surgical clip applier 1000 is shown. Handle assembly 1020 includes a housing 1030 having a first or right side half-section 1030a and a second or left side half-section 1030b. Handle assembly 1020 includes a trigger 1080 pivotably supported between right side half-section 1030a and left side half-section 1030b. Handle assembly 1020 defines a window 1030c formed in housing 1030 for supporting and displaying a counter mechanism, as will be discussed in greater detail below. Housing 1030 of handle assembly 1020 may be formed of a suitable plastic material.

Housing 1030 supports a drive assembly 1200 between right side half-section 1030a and left side half-section 1030b. Drive assembly 1200 includes a wishbone link 1220 having a first end pivotally connected to trigger 1080, and a second end pivotally connected to a crank plate 1240. As seen in FIGS. 13-16, drive assembly 1200 further includes a drive connector 1340 rotatably connected to crank plate 1240, a plunger 1350 interconnected to drive connector 1340, and a spring 1360 supported on drive connector 1340. Plunger 1350 defines a longitudinal slot 1350a configured and adapted to receive a proximal end of a drive bar 1400 therein.

Figure 16:
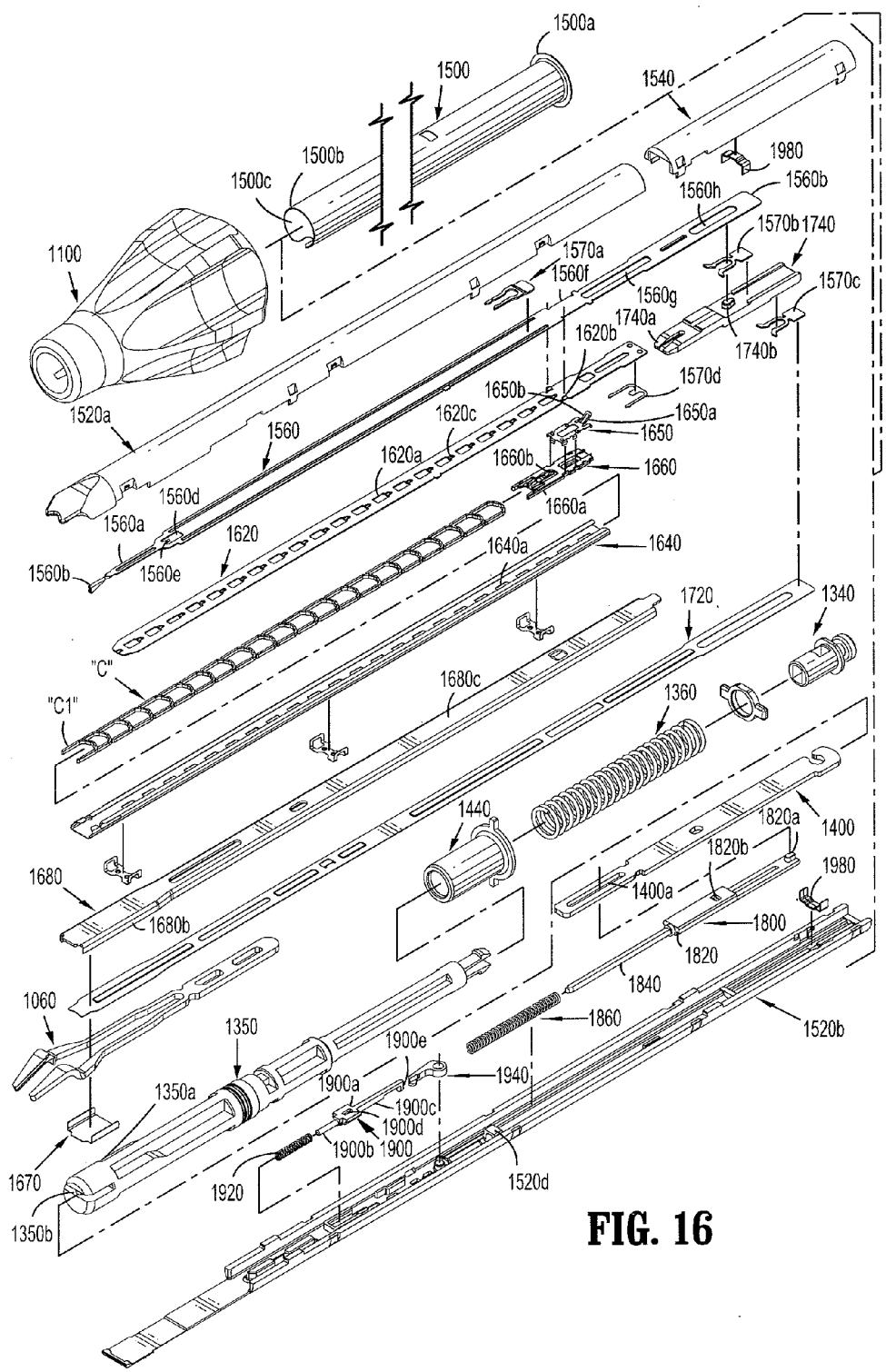
FIG. 16 is a perspective view, with parts separated, of the shaft assembly of the clip applier of FIGS. 8-12.

Drive bar 1400 is connected to plunger 1350 via an integral pin 1350b (see FIG. 16). A cap 1440 is provided through which plunger 1350 extends. A seal (not shown) is provided to create an air-tight seal between plunger 1350 and an outer tube 1500.

Figure 13:
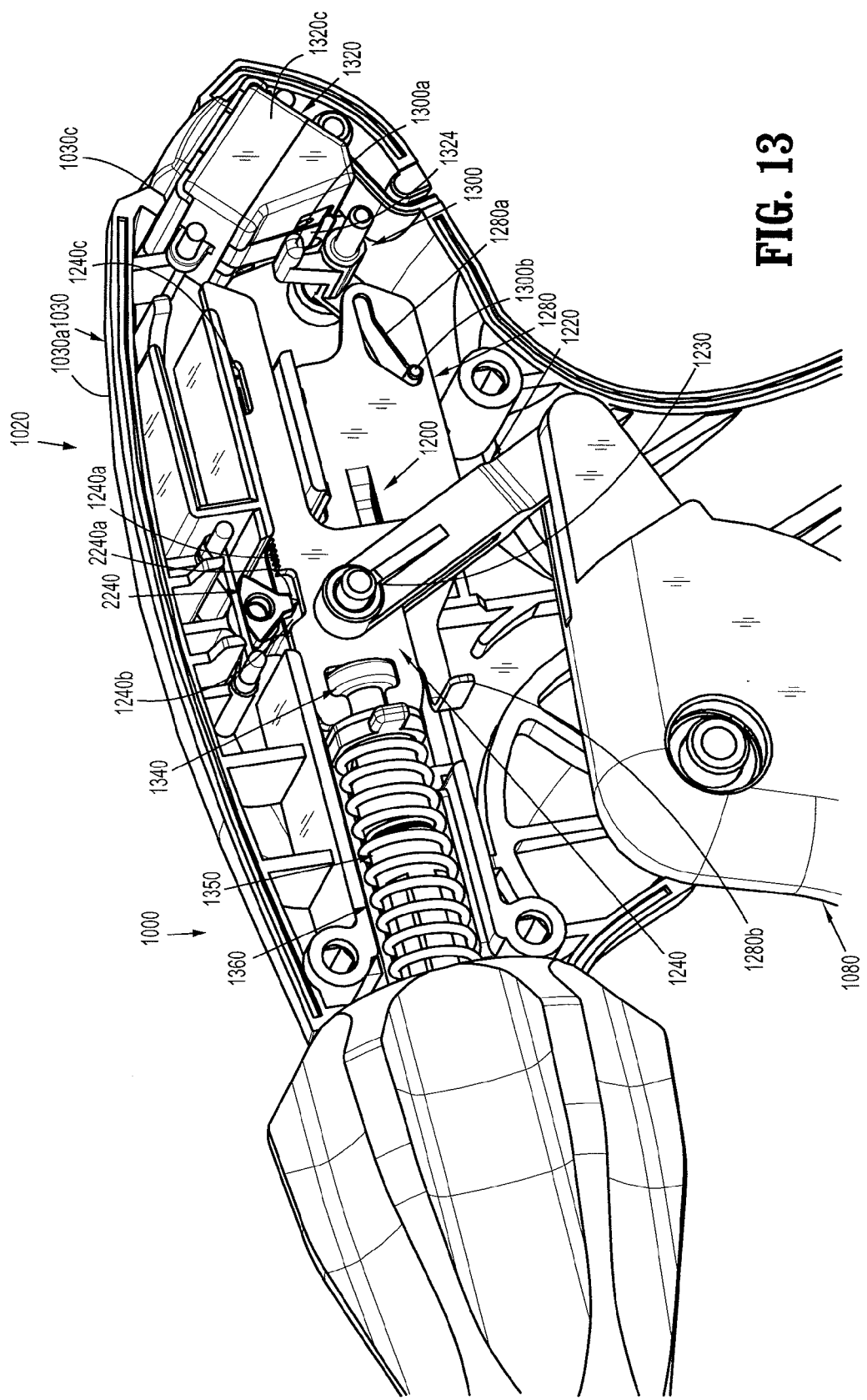
FIG. 13 is a perspective view of a handle assembly of the clip applier of FIG. 8-12, illustrated with a left side housing half-section removed therefrom.
Figure 14:
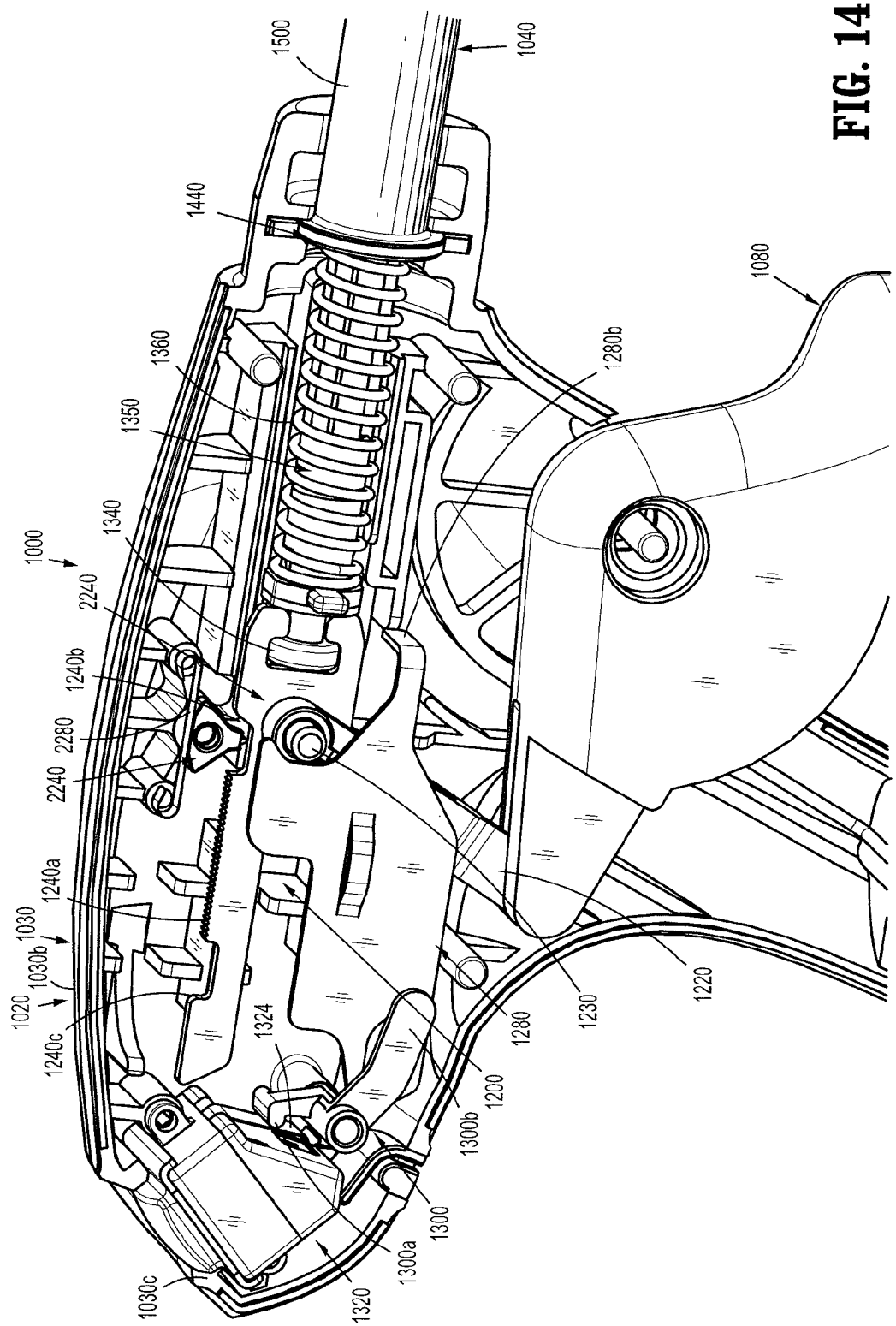
FIG. 14 is a perspective view of a handle assembly of the clip applier of FIG. 8-12, illustrated with a right side housing half-section removed therefrom.
Figure 15:
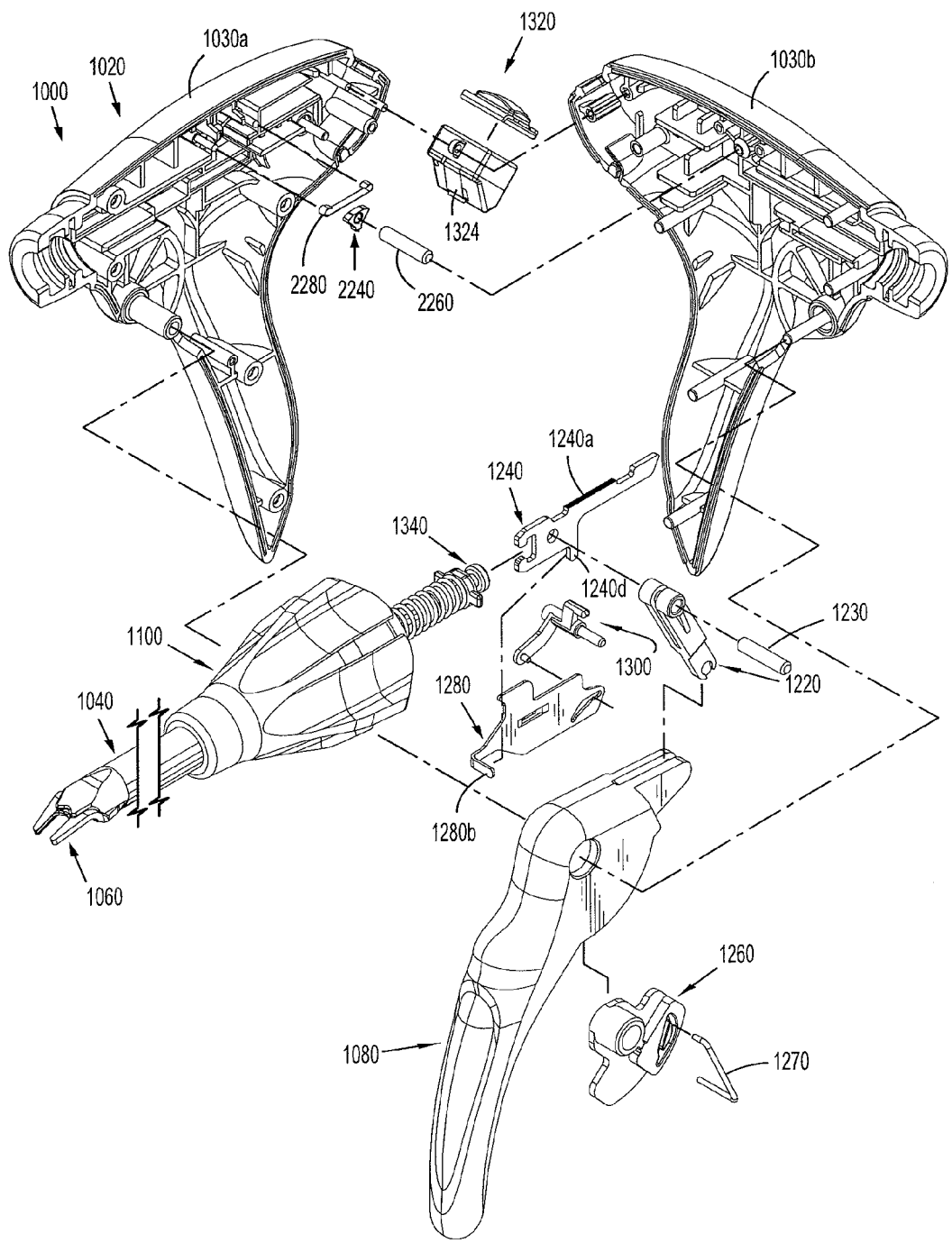
FIG. 15 is a perspective view, with parts separated, of the handle assembly of the clip applier of FIGS. 8-12.

As seen in FIGS. 13-15, handle assembly 1020 further includes a rack 1240a formed in/on crank plate 1240 such that rack 1240a is movable therewith. Rack 1240a includes a plurality of teeth interposed between a distal recess 1240b and a proximal recess 1240c defined in crank plate 1240. Recesses 1240b and 1240c are provided to allow pawl 2240 to reverse and advance back over the teeth of rack 1240a when crank plate 1240 changes between proximal and distal movement.

Handle assembly 1020 further includes a pawl 2240 pivotally connected to housing 1030 by a pawl pin 2260 at a location wherein pawl 2240 is in substantial operative engagement with rack 1240a of crank plate 1240. Pawl 2240 includes a pawl tooth 2240a which is selectively engageable with the teeth of rack 1240a of crank plate 1240. Pawl tooth 2240a is engageable with the rack teeth to restrict longitudinal movement of rack 1240*a* and, in turn, crank plate 1240 within handle assembly 1020. A pawl spring 2280 is provided to bias pawl 2240 into operative engagement with rack 1240*a* of crank plate 1240.

As seen in FIGS. 13-15, crank plate 1240 is pivotably connected to wishbone link 1220 via a pin 1230. Crank plate 1240 defines a series of ratchet teeth 1240*a* formed therein for selective engagement with pawl 2240.

Figure 15A:
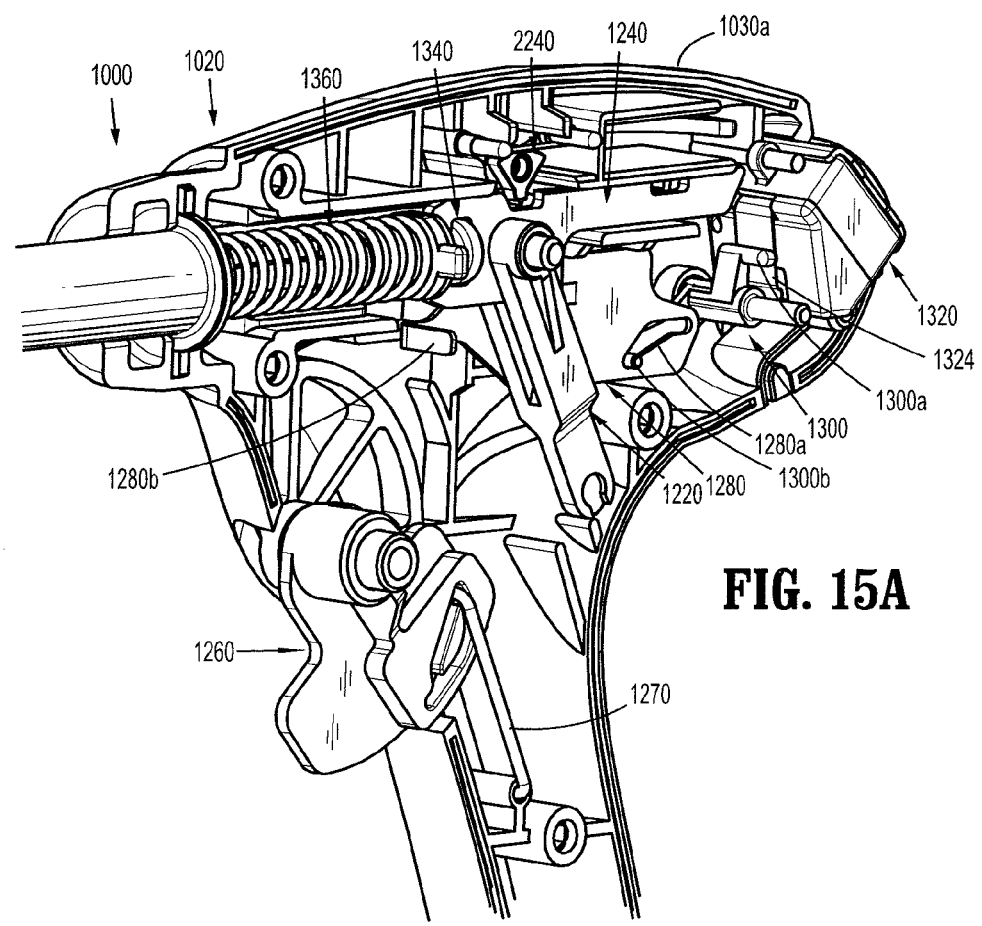
FIG. 15A is a perspective view of the handle assembly of FIGS. 13-15, with a trigger removed therefrom.
Figure 15B:
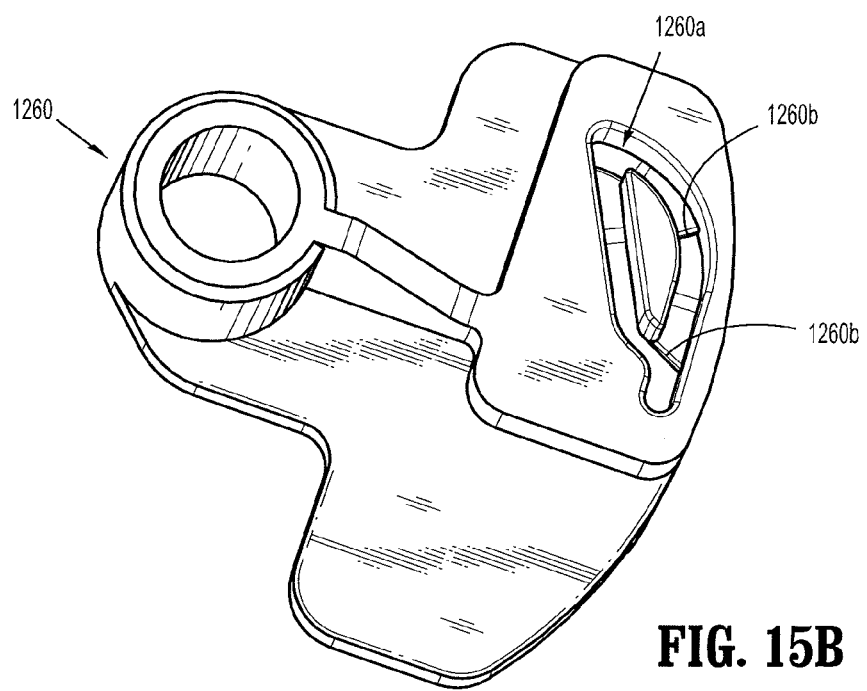
FIG. 15B is a perspective view of a feedback member of the handle assembly of FIGS. 13-15.

As seen in FIGS. 15, 15A and 15B, handle assembly 1020 further includes an audible/tactile feedback member 1260 operatively associated with trigger 1080 so as to rotate together with and about a common axis as trigger 1080 is actuated. Feedback member 1260 defines a race 1260*a* defining a plurality of ratchets or steps 1260*b*. A deflectable arm 1270 is provided and includes a first end operative connected or disposed in race 1260*a*, in contact with steps 1260*b*, of feedback member 1260 and a second end connected to housing 1030. In operation, as trigger 1080 is actuated, arm 1270 rides through and/or along race 1260*a* formed in feedback member 1260. As will be discussed in greater detail below, as arm 1270 moves over steps 1260*b* of feedback member 1260, arm 1270 snaps over steps 1260*b* and creates an audible sound/click and/or a tactile vibration.

Audible/tactile feedback member 1260 includes sufficient steps 1260*b* so as to create an audible/tactile indication after a clip has been fully loaded into the jaws of surgical clip applier 1000, after the loaded clip has been formed by the jaws of surgical clip applier 1000, and when surgical clip applier 1000 is reset to the home position and ready to fire/form another clip.

As seen in FIGS. 13, 14, 15 and 15A, handle assembly 1020 of surgical clip applier 1000 further includes a counter mechanism 1320 supported in housing 1030 and visible through window 1030*c* defined in housing 1030. Counter mechanism 1320 is similar to counter mechanism 190 and will be described in more detail below with reference to FIG. 17.

A Mylar or another polymeric insulating material is disposed between battery or energy source (not shown) and a contact of counter mechanism 1320 which prevents the battery or energy source from becoming drained during storage. The tab extends out of housing 1030 of surgical clip applier 1000 in order to allow for easy removal of the tab therefrom. Once the tab is removed, battery or energy source comes into electrical contact with the contact of counter mechanism 1320 and in turn actuates the counter mechanism.

As seen in FIGS. 13, 14, 15 and 15A, handle assembly 1020 of surgical clip applier 1000 further includes a counter actuation mechanism including a counter actuation lever 1300 having a first arm 1300*a* configured and adapted to operatively, selectively engage counter mechanism 1320. Counter actuation lever 1300 further includes a second arm 1300*b* configured and adapted to operatively, slidably engage a slot 1280*a* formed in an actuator plate 1280 slidably supported in housing 1030.

In operation, as will be described in greater detail below, as trigger 1080 is squeezed, trigger 1080 causes wishbone link 1220 to be advanced distally, causing crank plate 1240 to be advanced distally. When arm 1240*d* of crank plate 1240 is advanced a predetermined distance, arm 1240*d* engages or contacts finger 1280*b* of actuator plate 1280. As crank plate 1240 is further advanced distally, crank plate 1240 forces or pulls actuator plate 1280 in a distal direction thereby actuating counter actuation lever 1300 to activate counter mechanism 1320.

In particular, when actuator plate 1280 is moved distally a sufficient distance, second arm 1300*b* of counter actuation lever 1300 is cammed within slot 1280*b* thereof and rotates counter actuation lever 1300 resulting in first arm 1300*a* of counter actuation lever 130 engaging a switch 1324 of counter mechanism 1320. When actuator plate 1280 is moved proximally a sufficient distance, second arm 1300*b* of counter actuation lever 1300 is returned to a home position resulting in first arm 1300*a* of counter actuation lever 1300 disengaging counter mechanism 1320.

Turning now to FIG. 9, shaft assembly 1040 of surgical clip applier 1000 is shown and described hereinbelow. Shaft assembly 1040 and the components thereof may be formed of suitable biocompatible materials, such as, for example, stainless steel, titanium, plastics and the like. Shaft assembly 1040 includes an outer tube 1500 having a proximal end 1500*a* supported within housing 1030, a distal end 1500*b*, and a lumen 1500*c* extending therethrough. Outer tube 1500 is secured within housing 1030 by a flange projecting from an outer surface thereof. Shaft assembly 1040 further includes an upper housing 1520*a* and a lower housing 1520*b*, each disposed within lumen 1500*c* of outer tube 1500. A rear upper housing 1540 is disposed within outer tube 1500 and proximal of upper housing 1520*a*.

As seen in FIG. 16, shaft assembly 1040 further includes a pusher bar 1560 slidably disposed within upper housing 1520*a* and a rear upper housing 1540. Pusher bar 1560 includes a distal end 1560*a* defining a narrow-profile pusher 1560*c* configured and adapted to selectively engage/move (i.e., distally advance) a distal-most clip "C1" of a stack of clips "C" and to remain in contact with the distal-most clip "C1" during an initial formation thereof. Pusher bar 1560 further includes a proximal end 1560*b*. Pusher bar 1560 defines a distal window 1560*d* having a catch 1560*e*, a pair of recesses 1560*f* located proximal of distal window 1560*d* and framed in each side edge thereof, an elongate slot 1560*g* located proximal of side recesses 1560*f*, and a proximal-most window 1560*h* located proximal of slot 1560*g*.

As seen in FIG. 16, pusher bar 1560 supports a first snap clip 1570*a* along an upper surface thereof at a location distal of side recesses 1560*f* of pusher bar 1560. First snap clip 1570*a* is configured in such a manner that the tines thereof project or are spaced an amount from an upper surface of pusher bar 1560.

As seen in FIG. 16, pusher bar 1560 supports a second snap clip 1570*b* along a lower surface thereof at a location proximal of a proximal-most window 1560*h* of pusher bar 1560. Second snap clip 1570*b* is oriented in such a manner that the tines thereof project an amount sufficient to overlie proximal-most window 1560*h* of pusher bar 1560. The tines of second snap clip 1570*b* are spaced from one another by an amount that is less than a width of proximal-most window 1560*h* of pusher bar 1560.

As seen in FIG. 16, shaft assembly 1040 further includes an advancer plate 1620 reciprocally supported beneath pusher bar 1560. Snap clip 1570*d* includes a pair of tines that are detachably connected in proximal retaining grooves and distal retaining grooves formed in upper housing 1520*a*. In this manner, in use, snap clip 1570*d* detachably engage proximal retaining grooves and distal retaining grooves to maintain advancer plate 1620 in a proximal or a distal position. Upon distal advancement of advancer plate 1620, the tines of snap clip 1570*d* cam inward and allow advancer plate 1620 to continue to move distally.

As seen in FIG. 16, shaft assembly 1040 further includes a clip carrier 1640 disposed within upper housing 1520*a*, and beneath advancer plate 1620. Clip carrier 1640 is generally a box-like structure having an upper wall, a pair of side walls and a lower wall defining a channel therethrough. Clip carrier 1640 includes a plurality of spaced apart windows 1640*a* formed in the lower wall and extending longitudinally along a length thereof. Clip carrier 1640 includes an elongate window formed in the upper wall and extending longitudinally along a length thereof.

As seen in FIG. 16, a stack of surgical clips "C" is loaded and/or retained within the channel of clip carrier 1640 in a manner so as to slide therewithin and/or therealong. The channel of clip carrier 1640 is configured and dimensioned to slidably retain a stack or plurality of surgical clips "C" in tip-to-tail fashion therewithin.

As seen in FIG. 16, shaft assembly 1040 of clip applier 1000 further includes a clip follower 1660 slidably disposed within the channel of clip carrier 1640. Clip follower 1660 is positioned behind the stack of surgical clips "C" and is provided to urge the stack of clips "C" forward during an actuation of clip applier 1000. As will be described in greater detail below, clip follower 1660 is actuated by the reciprocating forward and backward motion of advancer plate 1620.

Distal tab 1660*b* of clip follower 1660 is configured and dimensioned to selectively engage ledges 1620*c* of windows 1620*a* of advancer plate 1620. In use, engagement of distal tab 1660*b* of clip follower 1660 against ledges 1620*c* of windows 1620*a* of advancer plate 1620 causes clip follower 1660 to incrementally advance or travel distally as advancer plate 1620 is advanced or moved in a distal direction. As seen in FIG. 16, a pair of side fins 1620*b* are slidably disposed within side recesses 1560*f* of pusher bar 1560.

Proximal tab 1660*c* is configured and dimensioned to selectively engage windows 1640*a* formed in clip carrier 1640. In use, engagement of proximal tab 1660*c* of clip follower 1660 in a window 1640*a* formed clip carrier 1640 prevents clip follower 1660 from traveling or moving in a proximal direction.

Clip follower 1660 includes a lock-out plate 1650 supported thereon or alternatively, integrally formed therewith. Lock-out plate 1650 includes a resilient tail 1650*a*, defining a window 1650*b*, extending therefrom, in a direction upwardly and rearwardly from body portion 1660*a* of clip follower 1660.

As seen in FIG. 16, shaft assembly 1040 further includes a drive channel 1680 reciprocally supported in channel assembly 1040 at a location below clip carrier 1640. Drive channel 1680 is a substantially U-shaped channel including a pair of spaced apart side walls 1680*b* extending from a backspan 1680*c* thereof, in a direction away from clip carrier 1640 and towards lower housing 1520*b*. Drive channel 1680 further includes a tab (not shown) projecting from backspan 1680*c*, at a location proximal of slot 1680*a*, and extending in the direction of side walls 1680*b*.

As seen in FIG. 16, shaft assembly 1040 of clip applier 1000 includes a drive channel strap 1670 secured to drive channel 1680. Strap 1670 is secured to side walls 1680*b* of drive channel 1680 so as to extend transversely thereacross. Strap 1670 is secured to drive channel 1680 at a location distal of elongate slot 1680*a*. Strap 1670 is secured to drive channel 1680 such that wedge plate 1720 extends between backspan 1680*c* of drive channel 1680 and jaws 1060.

As seen in FIG. 16, clip applier 1000 includes a pair of jaws 1060 mounted on or at a distal end of shaft assembly 1040 and actuatable by trigger 1080. Jaws 1060 are formed of a suitable biocompatible material such as, for example, stainless steel or titanium.

Jaws 1060 are mounted adjacent a distal end of drive channel 1680, via bosses formed in lower housing 1520*b* that engage receiving slots formed in jaws 1060, such that jaws 1060 are held stationary relative to drive channel 168.

As seen in FIG. 16, shaft assembly 1040 of clip applier 1000 further includes a wedge plate 1720 having a distal end interposed between drive channel 1680 and jaws 1060 and a proximal end extending through shaft assembly 1040. Wedge plate 1720 includes a substantially tapered distal end 1720*a* for selective operative interposition between jaws 1060. As seen in FIG. 26, wedge plate 1720 defines a fin or tab 1720*b* projecting from a lower surface thereof.

As seen in FIG. 16, shaft assembly 1040 of clip applier 1000 further includes a connector plate 1740 slidably interposed between pusher bar 1560 and wedge plate 1720 and detachably connectable to each of pusher bar 1560 and wedge plate 1720. Connector plate 1740 includes a tapered distal end 1740*a*, a first stem 1740*b* extending from an upper surface thereof and a second stem (not shown) extending from a bottom surface thereof. Each stem has a substantially teardrop shaped profile wherein a distal end of each stem is larger than a proximal end thereof.

In operation, first stem 1740*b* of connector plate 1740 is configured and dimensioned for detachable connection with second snap clip 1570*b* that is secured to pusher bar 1560, and the second stem (not shown) of connector plate 1740 is configured and dimensioned for detachable connection with third snap clip 1570*c* that is secured to wedge plate 1720.

As seen in FIG. 16, a guard 1980 is supported in lower housing 1520*b* at a location so as to maintain the relative distance between the tines of the third snap-clip 1570*c* during an initial distal advancement thereof. In this manner, second stem 1740*b* of connector plate 1740 can not prematurely disengage from third snap clip 1570*c* until third snap clip 1570*c* has surpassed guard 1980.

As seen in FIG. 16, shaft assembly 1040 of clip applier 1000 further includes a slider joint 1800 slidably supported within a channel of lower housing 1520*b*. Slider joint 1800 includes a body portion 1820 and a rod 1840 extending therefrom. When properly positioned within the channel of lower housing 1520*b*, rod 1840 of slider joint 1800 extends in a substantially distal direction. Rod 1840 of slider joint 1800 slidably passes through a stub 1520*d* foamed in and extending from the channel of lower housing 1520*b* (see FIG. 29). Shaft assembly 1040 further includes a biasing member 1860, in the form of a compression spring, supported on rod 1840 and interposed between stub 1520*d* of lower housing 1520*b* and body portion 1820 of slider joint 1800.

Body portion 1820 of slider joint 1800 includes a boss 1820*a* formed near a proximal end thereof, and configured and adapted for slidable engagement in elongate slot 1400*a* of drive bar 1400. Body portion 1820 of slider joint 1800 further includes a pocket 1820*b* formed near a distal end thereof, and configured and adapted for receiving the tab of drive channel 1680 therein.

As seen in FIG. 16, shaft assembly 1040 of clip applier 1000 further includes a wedge plate lock 1900 slidably supported in the channel of lower housing 1520*b* and in drive channel 1680. Wedge plate lock 1900 includes a body portion 1900*a*, a rod 1900*b* extending distally from body portion 1900*a*, a tail 1900*c* extending proximally from body portion 1900*a*, a pocket 1900*d* formed in an upper surface of body portion 1900*a*, and a stem or tooth 1900*e* extending from tail 1900*c*. Shaft assembly 1040 further includes a biasing member 1920, in the form of a compression spring, supported on rod 1900*b* and interposed between lower housing 1520*b* of and body portion 1900*a* of wedge plate lock 1900.

Shaft assembly 1040 of clip applier 1000 further includes a wedge plate release 1940 rotatably supported in the channel of lower housing 1520*b*. Wedge plate release 1940 includes a stem configured for engagement with tooth 1900*e* extending from tail 1900c of wedge lock plate 1900, a hammer extending outwardly from the stem in a direction toward tail 1900c of wedge plate lock 1900, and a tooth extending outwardly from the stem in a direction away from tail 1900c of wedge plate lock 1900.

Figure 17:
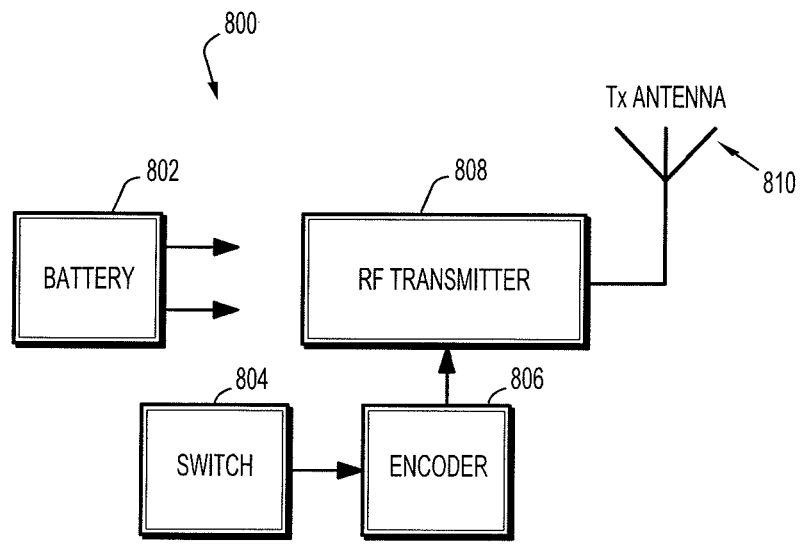
FIG. 17 is a schematic block diagram of a counter mechanism of the surgical clip applier.

As seen in FIG. 17, a counter mechanism in accordance with an embodiment of the present disclosure is generally designated as 800. Counter mechanism 800 transmits a signal to a display unit 900 (FIG. 18) to display a number of clips. Counter mechanism 800 includes a battery 802 that provides power to the circuitry in counter mechanism 800. Battery 802 may be replaced with a power supply that converts an alternating current (AC) power source to a direct current (DC) power source. Counter mechanism 800 includes a switch 804. When switch 804 is actuated as described above (in the manner of switch 194 of counter mechanism 190 of clip applier 100 and/or switch 1324 of counter mechanism 1320 of clip applier 1000), switch 804 completes a circuit which provides a signal or pulse to encoder 806. Encoder 806 may provide a bit sequence having a single bit to indicate that the switch 804 has been activated or a bit sequence having at least two bits to indicate that the switch 804 is inactive. The bit sequence may have a header identifying the clip applier being used by the clinician or the display that will receive the transmitted bit or bit sequence, a data portion indicating that a clip has been applied and/or an error correction code to determine if the signal to be transmitted by counter mechanism 800 is correct. Encoder 806 provides the bit or bit sequence to a radio frequency (RF) transmitter 808. RF transmitter 808 converts the signal into an RF signal and transmits the RF signal via transmitting antenna 810.

Figure 18:
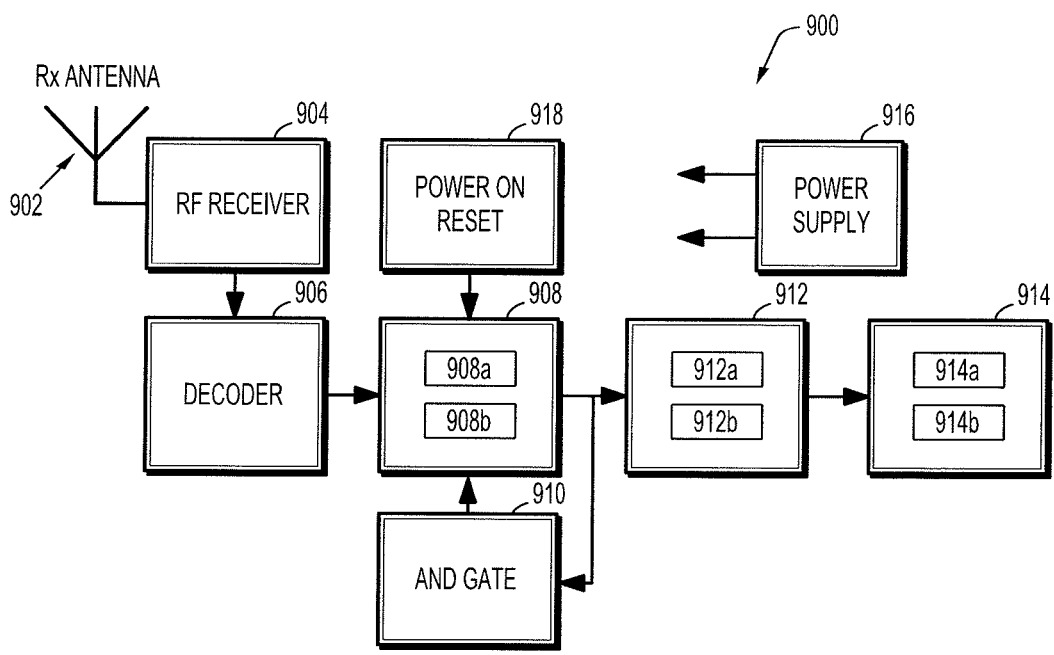
FIG. 18 is a schematic block diagram of a remote display associated with the surgical clip applier.
Figure 19:
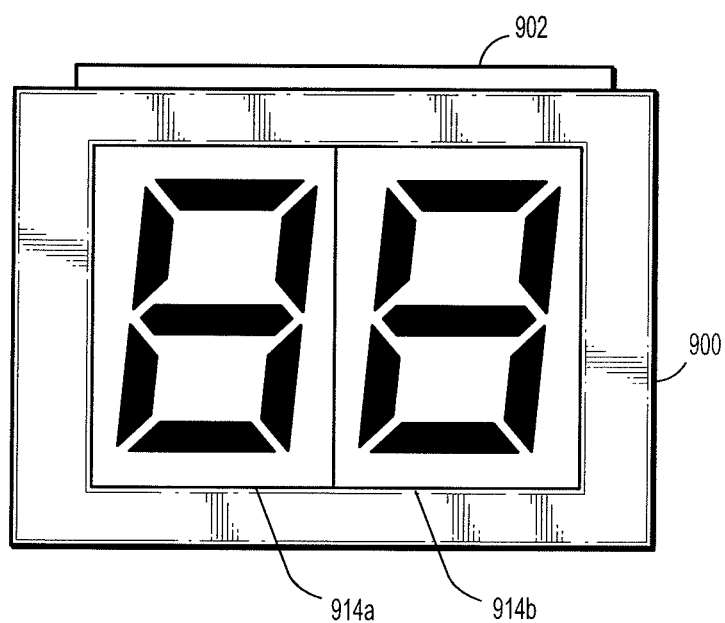
FIG. 19 is a front view illustrating the remote display of FIG. 18.

As seen in FIGS. 18 and 19, a display unit in accordance with an embodiment of the present disclosure is generally designated as 900. Display unit 900 includes a receiving antenna 902 that receives the RF signal from transmitter 808 of counter mechanism 800 and forwards the RF signal to an RF receiver 904. RF receiver 904 receives the RF signal and converts the RF signal to a bit sequence. The bit sequence is provided to a decoder 906 which decodes the bit sequence. Decoder 906 may determine that display unit 900 is the correct display unit to receive the bit sequence using the header information. Decoder 906 may also determine that the received bit sequence is error free and if the received bit sequence does contain an error, decoder 906 may correct the error or request re-transmission of the bit sequence from counter mechanism 800.

Decoder 906 provides a signal or pulse to binary coded decimal (BCD) counter 908. BCD counter 908 includes BCD counter 908a to count in tens and BCD counter 908b to count in ones. When display unit 900 is powered "ON" a default number representing a number of clips in the clip applier may be stored therein in a memory (not shown). When BCD counter 908 receives a signal from decoder 906, the BCD counter either increments or decrements the default number by one. For instance, when BCD counter 908 receives a signal, a second BCD counter 908b may increment the count by one. When the count in the second BCD counter 908b reaches ten, for example, the count in a first BCD counter 908a is incremented by one. On the other hand if the count is decremented, when BCD counter 908 receives a signal, the second BCD counter 908b may decrement the count by one. When the count in the second BCD counter 908b reaches zero, the count in the first BCD counter 908a is decremented by one.

BCD counter 908 provides a binary coded signal to BCD decoder/driver 912. BCD decoder/driver 912 includes a first BCD decoder/driver 912a which receives a signal from the first BCD counter 908a and a second BCD decoder/driver 912b which receives a signal from the second BCD counter 908b. BCD decoder/driver 912 decodes the received binary coded signal and outputs the signal to a display 914. Display 914 displays one or more operating parameters of clip applier to the surgeon. The operating parameter displayed by display 914 includes an amount or number of clips remaining, a number of clips that have been used or any other parameter of the procedure. Display 914 includes a pair of seven segment light emitting diodes (LEDs) 914a and 914b. First LED 914a displays the tens digit provided by first BCD decoder/driver 912a and second LED 914b displays the ones digit provided by second BCD decoder/driver 912b.

Display unit 900 is powered by a power supply 916. Power supply 916 may be connected to an AC source such as a 110 v/220 v wall source or any other source. Power supply 916 is capable of converting the AC source to a DC voltage sufficient enough to power the components of the display unit 900. Alternatively, power supply 916 may include one or more batteries in series or parallel to supply sufficient power to the components of the display unit 900.

A "POWER ON"/"RESET" switch 918 is also provided in display unit 900. When the count displayed on display 914 reaches zero or some predetermined number, switch 918 may be used to reset the display 914 to the default number stored in the display unit 900 or to zero. An "AND" gate 910 may also be provided so that when the count in BCD counter 908 reaches zero for both BCD counters 908a and 908b, AND gate 910 retains the count at zero.

The embodiments described herein are merely illustrative and are not intended to limit the scope of the application. It should be readily appreciated by one skilled in the art that the presently described embodiments can be utilized in a wide variety of surgical clip appliers. For instance, U.S. patent application Ser. No. 12/406,345, the contents of which are also hereby incorporated by reference in its entirety, uses an optical path in the surgical clip applier, when the path is broken, a signal may be provided to a counter mechanism to increment or decrement the count.

Further, the display unit may include a microprocessor that performs all the functions of the components described above and output a signal to the display. The display might be have any number of seven segment LEDs to accommodate any number of digits or may be a liquid crystal display.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. An apparatus for application of surgical clips to body tissue, the apparatus comprising:
    a housing;
    at least one handle pivotably connected to the housing;
    a channel assembly extending distally from the housing;
    a clip carrier disposed within the channel assembly and defining a channel and a plurality of windows therein; and
    a counter mechanism supported in at least one of the housing and the channel assembly, wherein the counter mechanism is configured to transmit a change in status of the apparatus upon each actuation of the at least one handle, wherein the counter mechanism comprises:
  a switch configured to output a signal upon actuation of the at least one handle;
  an encoder configured to output a bit sequence upon actuation of the switch;
  a radio frequency transmitter operable to convert the bit sequence into a radio frequency signal; and
  a transmitting antenna configured to transmit the radio frequency signal.

2. An apparatus for application of surgical clips to body tissue, the apparatus comprising:
  a handle assembly having a trigger;
  a shaft assembly including a housing extending distally from the handle assembly and defining a longitudinal axis;
  a jaw mounted adjacent a distal end portion of the shaft assembly, the jaw being movable between an open spaced-apart condition and a closed approximated condition; and
  a counter mechanism supported in the handle assembly, wherein the counter mechanism provides an indication when a surgical clip has been fired upon activation of the trigger, wherein the counter mechanism comprises:
    a switch configured to output a signal upon actuation of the trigger;
    an encoder configured to output a bit sequence upon actuation of the switch;
    a radio frequency transmitter operable to convert the bit sequence into a radio frequency signal; and
    a transmitting antenna configured to transmit the radio frequency signal.

* * * * *